United States Patent
Agarwal

(10) Patent No.: US 9,710,071 B2
(45) Date of Patent: Jul. 18, 2017

(54) METHODS AND SYSTEMS FOR RECALIBRATING A USER DEVICE BASED ON AGE OF A USER AND RECEIVED VERBAL INPUT

(71) Applicant: United Video Properties, Inc., Santa Clara, CA (US)

(72) Inventor: Akshat Agarwal, Delhi (IN)

(73) Assignee: Rovi Guides, Inc., San Carlos, CA (US)

( * ) Notice: Subject to any disclaimer, the term of this patent is extended or adjusted under 35 U.S.C. 154(b) by 90 days.

(21) Appl. No.: 14/492,377

(22) Filed: Sep. 22, 2014

(65) Prior Publication Data

US 2016/0085317 A1   Mar. 24, 2016

(51) Int. Cl.
G06F 3/03 (2006.01)
G06F 3/01 (2006.01)
G06F 3/16 (2006.01)

(52) U.S. Cl.
CPC ............. G06F 3/03 (2013.01); G06F 3/015 (2013.01); G06F 3/017 (2013.01); G06F 3/167 (2013.01)

(58) Field of Classification Search
CPC . G06F 3/03; G06F 3/015; G06F 3/017; G06F 3/167
See application file for complete search history.

(56) References Cited

U.S. PATENT DOCUMENTS

| | | | |
|---|---|---|---|
| 6,239,794 B1 | 5/2001 | Yuen et al. | |
| 6,388,714 B1 | 5/2002 | Schein et al. | |
| 6,564,378 B1 | 5/2003 | Satterfield et al. | |
| 6,756,997 B1 | 6/2004 | Ward, III et al. | |
| 7,165,098 B1 | 1/2007 | Boyer et al. | |
| 7,761,892 B2 | 7/2010 | Ellis et al. | |
| 8,046,801 B2 | 10/2011 | Ellis et al. | |
| 8,332,883 B2 | 12/2012 | Lee et al. | |
| 8,373,768 B2 | 2/2013 | Bill | |
| 2002/0138743 A1 | 9/2002 | Murakami et al. | |
| 2002/0174430 A1 | 11/2002 | Ellis et al. | |
| 2003/0110499 A1 | 6/2003 | Knudson et al. | |
| 2005/0251827 A1 | 11/2005 | Ellis et al. | |
| 2006/0080102 A1* | 4/2006 | Roy | G10L 13/08 704/260 |
| 2007/0177770 A1 | 8/2007 | Derchak et al. | |
| 2009/0175968 A1* | 7/2009 | Ivie | A61K 31/70 424/752 |
| 2010/0153885 A1 | 6/2010 | Yates | |
| 2012/0029322 A1 | 2/2012 | Wartena et al. | |

(Continued)

OTHER PUBLICATIONS

Frank et al., "Biofeedback in medicine: who, when, why and how?" Ment. Health Fam. Med., Jun. 2010.

(Continued)

*Primary Examiner* — Ryan A Lubit

(74) *Attorney, Agent, or Firm* — Ropes & Gray LLP

(57) ABSTRACT

Methods and systems are described herein for a media guidance application that enhances the precision of various types of user input interfaces. For example, the media guidance application may recalibrate a user input interface such that the user inputs are correctly received and executed. Furthermore, to further enhance precision, the media guidance application may base the recalibrations on the age of a user.

20 Claims, 6 Drawing Sheets

(56) References Cited

U.S. PATENT DOCUMENTS

| | | | | |
|---|---|---|---|---|
| 2012/0112995 | A1* | 5/2012 | Maeda | G06F 3/017 |
| | | | | 345/156 |
| 2013/0080182 | A1* | 3/2013 | Kovach | C12Q 1/6883 |
| | | | | 705/2 |
| 2014/0009378 | A1* | 1/2014 | Chew | G06F 3/017 |
| | | | | 345/156 |
| 2014/0092018 | A1* | 4/2014 | Geithner | G06F 3/013 |
| | | | | 345/160 |
| 2014/0172314 | A1* | 6/2014 | Baarman | A61B 5/0537 |
| | | | | 702/19 |
| 2014/0255887 | A1* | 9/2014 | Xu | A61B 5/7264 |
| | | | | 434/169 |
| 2014/0310271 | A1* | 10/2014 | Song | G06K 9/00288 |
| | | | | 707/732 |
| 2015/0029087 | A1 | 1/2015 | Klappert et al. | |
| 2015/0032873 | A1* | 1/2015 | Chen | H04L 67/22 |
| | | | | 709/224 |
| 2015/0033245 | A1 | 1/2015 | Klappert et al. | |
| 2015/0033258 | A1 | 1/2015 | Klappert et al. | |
| 2015/0033259 | A1 | 1/2015 | Klappert et al. | |
| 2015/0033262 | A1 | 1/2015 | Klappert et al. | |
| 2015/0033266 | A1 | 1/2015 | Klappert et al. | |
| 2015/0137937 | A1* | 5/2015 | Smith | G07C 9/00158 |
| | | | | 340/5.52 |
| 2015/0220513 | A1* | 8/2015 | Lyman | G10L 15/18 |
| | | | | 704/9 |

OTHER PUBLICATIONS

Rybak, "Frontal Alpha Power Asymmetry in Aggressive Children and Adolescents With Mood and Disruptive Behavior Disorders," Clinical EEL and Neuroscience, vol. 3, 2006.

* cited by examiner

METHODS AND SYSTEMS FOR RECALIBRATING A USER DEVICE BASED ON AGE OF A USER AND RECEIVED VERBAL INPUT

BACKGROUND

Current systems offer users multiple ways to interact with devices (e.g., keyboards, touchscreens, and/or voice controls). While inputs entered via dedicated buttons (e.g., keys on a keyboard) may offer enhance precision, such devices also require hand-operation by a user. However, in many cases hands-free operation is preferred by the user, even if enhance precision is sacrificed.

SUMMARY

Accordingly, methods and systems are described herein for a media guidance application that enhances the precision of various types of user input interfaces. For example, the media guidance application may recalibrate a user input interface such that the user inputs are correctly received and executed. Furthermore, to further enhance precision, the media guidance application may base the recalibrations on the age of a user.

For example, while user input interfaces that accept inputs as voice commands, motion-sensitive commands, fluctuations of brain activity, etc. offer users greater freedom and hands-free operation, the media guidance application may recalibrate (or determine a rate at which to recalibrate) inputs, user input interfaces, and/or user profiles based on the age of a user in order to compensate for changes to the voice, coordination, brain activity, etc. of the user at the age of the user.

For example, the media guidance application may maintain a calibration for a user input interface (or a particular input) for a particular user. The media guidance application may periodically recalibrate the user input interface accordingly to a schedule that is based on the age of the user. For example, during ages of the user at which changes to the user occur more frequently (e.g., puberty), the media guidance application may recalibrate the user input interface (or a particular input) at a higher frequency.

In some aspects, the media guidance application may store (e.g., in storage circuitry) a calibration of an input for a user. For example, the media guidance application may store a calibration for an input (or a user input interface) in a user profile associated with a user. The calibration may indicate particular adjustments to data received from a user and/or instruments used to receive data from the user that may increase the precision at which inputs are received and/or processed.

The media guidance application may determine (e.g., using control circuitry) an age of the user. For example, upon creating a user profile, the media guidance may record an initial age of the user (e.g., based on one or more user queries). The media guidance application may continuously or periodically update the age of the user in order to determine the current age of the user.

The media guidance application may then cross-reference (e.g., using control circuitry) the age of the user with a database (e.g., located in storage circuitry) listing recalibration rates at which inputs need to be recalibrated for given ages to determine a recalibration rate at which to recalibrate the calibration. For example, in response to determining that a user is a particular age, the media guidance application may determine the rate at which an input, user input interface, and/or user profile associated with a user of that particular age should be recalibrated.

The media guidance application may then recalibrate (e.g., using control circuitry) the calibration at the recalibration rate. For example, in response to determining that the calibration of the input should be recalibrated once a week for a user of the particular age of the user, the media guidance application may recalibrate an input, a user input interface, and/or a user profile associated with the user if the input, user input interface, and/or user profile has not been recalibrated within a week.

In some embodiments, the media guidance application may determine a length of time since a previous recalibration and compare the recalibration rate to the length of time to determine whether or not the calibration needs to be recalibrated. For example, the media guidance application may determine that the recalibration rate should correspond to a recalibration after a particular length of time. The media guidance application may then determine whether or not the length of time from the current point in time to the point in time of the last recalibration (if any) is greater than or equal to the particular length of time.

In some embodiments, the media guidance application may further indicate to a user when a recalibration should be performed. For example, in response to determining the calibration needs to be recalibrated, the media guidance application may notify the user. The media guidance application may then automatically, without a user input, recalibrate an input, user input interface, and/or user profile, or wait until a user requests the recalibration.

In another example, the media guidance application may recalibrate an input, user input interface, and/or user profile based on an age of a user in response to failing to recognize an input. For example, the media guidance application may detect the receipt of an input of a particular type (e.g., a voice command). However, the media guidance application may determine that the particular voice command does not correspond to any available media guidance application operations and/or does not correspond to a user (e.g., the voice of a user) associated with a current user profile. In response, the media guidance application may recalibrate the input, user input interface, and/or user profile based on the age of a user in order to determine whether or not the input is recognized after the recalibration.

In some aspects, the media guidance application may receive an input. For example, the media guidance application may receive inputs via voice controls, motion controls, brain activity controls, etc. through one or more user input interfaces.

The media guidance application may determine whether or not the input corresponds to a first user profile for a first user. For example, the media guidance application may compare the input (or the measurements associated with the input) to a user profile. For example, a voice command may include a particular accent, pronunciation, articulation, roughness, nasality, pitch, volume, and speed. The media guidance application may interpret the command based on the degrees of these various factors in a user profile.

The media guidance application, in response to determining that the input does not correspond to the first user profile, may recalibrate the first user profile based on an age of the user. For example, in response to determining that there is a discrepancy in the accent, pronunciation, etc. between a received voice command and the correct accent, pronunciation, etc. in a user profile (e.g., causing the command or the user issuing the command to fail to be recognized), the media guidance application may recalibrate the user profile in order to alleviate the discrepancy.

The media guidance application may then determine whether the input corresponds to the recalibrated first user profile. For example, in response to determining that the pitch of a received voice command differs from the pitch associated with voice commands in the first user profile, the media guidance application may recalibrate the first user profile based on the age of the user. In such cases, the media guidance application may determine that, based on the age of the user, the pitch in the user profile should be lowered. Accordingly, the media guidance application may lower the pitch associated with voice commands in the first user profile. After which, the media guidance application may determine whether the pitch of the received voice command corresponds to the lowered pitch associated with the recalibrated user profile.

The media guidance application may accept the input in response to determining that the input corresponds to the recalibrated first user profile. For example, in response to determining that the pitch of the received voice command corresponds to the lowered pitch associated with the recalibrated user profile, the media guidance application may perform (or cause to be performed) the received voice command. Alternatively, the media guidance application may not accept the input in response to determining that the input does not correspond to the recalibrated first user profile. For example, in response to determining that the pitch of the received voice command does not correspond to the lowered pitch associated with the recalibrated user profile, the media guidance application may not perform (or cause to be performed) the received voice command.

In some embodiments, the media guidance application may create a second user profile for a current user in response to determining that the input does not correspond to the recalibrated first user profile. For example, in response to determining that the pitch of the received voice command does not correspond to the lowered pitch associated with the recalibrated user profile, the media guidance application may determine that the current user is not the same user as the user associated with the first user profile. Accordingly, the media guidance application may automatically, without user input, create a second user profile for the current user. Alternatively, the media guidance application may not create a second user profile until a user request for the creation of the second user profile is received.

In some embodiments, if a second user profile is created by the media guidance application, the media guidance application may query the current user to determine the name, age, or other information about the current user. For example, when creating the second user profile, the media guidance application may request the current user identify himself or herself.

It should be noted that the systems and/or methods described above may be applied to, or used in accordance with, other systems, methods and/or apparatuses.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which.

DETAILED DESCRIPTION OF THE DRAWINGS

Figure 1:
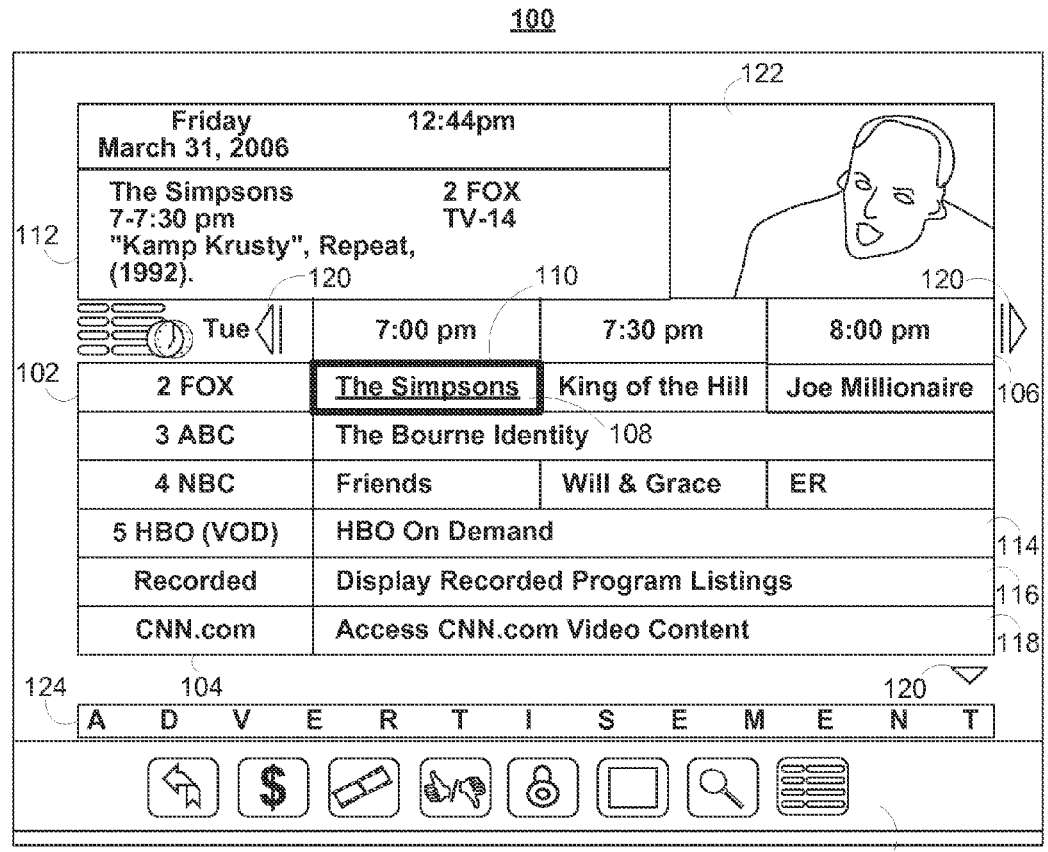
FIG. 1 shows an illustrative example of a display screen generated by a media guidance application in accordance with some embodiments of the disclosure.

Methods and systems are described herein for a media guidance application that enhances the precision of various types of user input interfaces. For example, the media guidance application may recalibrate a user input interface such that the user inputs are correctly received and executed. Furthermore, to further enhance precision, the media guidance application may base the recalibrations on the age of a user. For example, while user input interfaces that accept inputs as voice commands, motion-sensitive, commands, fluctuations of brain activity, etc. offer users greater freedom and hands-free operation, the media guidance application may recalibrate (or determine a rate at which to recalibrate) inputs, user input interfaces, and/or user profiles based on the age of a user in order to compensate for changes to the voice, coordination, brain activity, etc. of the user at the age of the user.

Thus, it should be noted that, throughout this disclosure, numerous embodiments may be discussed. Furthermore, some embodiments may refer to the calibration and/or recalibration of an input, user input interface, and/or a user profile. It should be noted that any embodiment associated with a calibration and/or recalibration of an input, user input interface, and/or user profile may equally be applied to any other embodiment associated with the calibration of an input, user input interface, and/or user profile. For example, an embodiment related to recalibrating a input may equally be applied to an embodiment recalibrating a user profile.

As referred to herein, an "interactive media guidance application" or, sometimes, a "media guidance application" or a "guidance application" is an application that allows users to efficiently navigate and/or access media content through an interface. Interactive media guidance applications may take various forms depending on the content for which they provide guidance. One typical type of media guidance application is an interactive television program guide. Interactive television program guides (sometimes referred to as electronic program guides) are well-known guidance applications that, among other things, allow users to navigate among and locate many types of content or media assets. Interactive media guidance applications may generate graphical user interface screens that enable a user to navigate among, locate and select content.

In some embodiments, the media guidance application and/or any instructions for performing any of the embodiments discussed herein may be encoded on computer readable media. Computer readable media includes any media capable of storing data. The computer readable media may be transitory, including, but not limited to, propagating electrical or electromagnetic signals, or may be non-transitory including, but not limited to, volatile and nonvolatile computer memory or storage devices such as a hard disk, floppy disk, USB drive, DVD, CD, media cards, register memory, processor caches, Random Access Memory ("RAM"), etc.

For example, a media guidance application may be implemented on, or otherwise control, a user device that is used to present media content. For example, the user device could be used to present a presentation. Furthermore, the presentation of the media content may be controlled through user commands (e.g., motion and/or voice controls) issued from a presenter of the presentation. The media guidance application may distinguish between the presenter and members of the audience based on gestures made by the audience in order to prevent the detection of false-positive user commands (e.g., triggered based on audience member conversations).

As referred to herein, the terms "media asset" and "content" should be understood to mean an electronically consumable user asset, such as television programming, as well as pay-per-view programs, on-demand programs (as in video-on-demand (VOD) systems), Internet content (e.g., streaming content, downloadable content, Webcasts, etc.), video clips, audio, content information, pictures, rotating images, documents, playlists, websites, articles, books, electronic books, blogs, advertisements, chat sessions, social media, applications, games, and/or any other media or multimedia and/or combination of the same. Guidance applications also allow users to navigate among and locate content. As referred to herein, the term "multimedia" should be understood to mean content that utilizes at least two different content forms described above, for example, text, audio, images, video, or interactive content forms. Content may be recorded, played, displayed or accessed by user equipment devices, but can also be part of a live performance.

Media guidance application may allow users to perform one or more media guidance application operations. As referred to herein, a "media guidance application operation" refers to any operation performed by a media guidance application. For example, a media guidance application operation may correspond to providing, receiving, and/or generating for display media assets and/or media guidance data for consumption by a user. For example, media guidance application operations include displaying media guidance data, providing options to navigate, select, and edit media guidance data or content (e.g., a media asset) associated with media guidance data, and/or manipulating a device used to access (e.g., a display device), retrieve (e.g., a server), and/or associate media guidance data with a user (e.g., a user device for monitoring brain activity).

One of the functions of the media guidance application is to provide media guidance data to users. As referred to herein, the phrase "media guidance data" or "guidance data" should be understood to mean any data related to content or data used in operating the guidance application. For example, the guidance data may include program information, guidance application settings, user preferences, user profile information, media listings, media-related information (e.g., broadcast times, broadcast channels, titles, descriptions, ratings information (e.g., parental control ratings, critic's ratings, etc.), genre or category information, actor information, logo data for broadcasters' or providers' logos, etc.), media format (e.g., standard definition, high definition, 3D, etc.), advertisement information (e.g., text, images, media clips, etc.), on-demand information, blogs, websites, and any other type of guidance data that is helpful for a user to navigate among and locate desired content selections.

Other operations of a media guidance application are to play media assets and provide fast access playback operations for those media assets. As referred to herein, the phrase "fast-access playback operations" should be understood to mean any media guidance application operation that pertains to playing back a non-linear media asset faster than normal playback speed or in a different order than the media asset is designed to be played, such as a fast-forward, rewind, skip, chapter selection, segment selection, skip segment, jump segment, next segment, previous segment, skip advertisement or commercial, next chapter, previous chapter or any other operation that does not play back the media asset at normal playback speed. The fast-access playback operation may be any playback operation that is not "play," where the play operation plays back the media asset at normal playback speed.

Still other operations of a media guidance application may include the control of user devices. For example, a media guidance application operation may include turning a device on and off, raising the volume associated with a device, adjusting the display settings of a device, assigning parental controls, transferring information (e.g., messages) from one device to another, storing and/or recording content, entering authorization information and/or payment information, etc.

With the advent of the Internet, mobile computing, and high-speed wireless networks, users are accessing media on user equipment devices which they traditionally did not use. As referred to herein, the phrase "user equipment device," "user equipment," "user device," "electronic device," "electronic equipment," "media equipment device," or "media device" should be understood to mean any device for accessing the content described above, such as a television, a Smart TV, a set-top box, an integrated receiver decoder (IRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a hand-held computer, a stationary telephone, a personal digital assistant (PDA), a mobile telephone, a portable video player, a portable music player, a portable gaming machine, a smart phone, or any other television equipment, computing equipment, or wireless device, and/or combination of the same.

In some embodiments, the user equipment device may have a front facing screen and a rear facing screen, multiple front screens, or multiple angled screens. In some embodiments, the user equipment device may have a front facing camera and/or a rear facing camera. On these user equipment devices, users may be able to navigate among and locate the same content available through a television. Consequently, media guidance may be available on these devices, as well. The guidance provided may be for content available only through a television, for content available only through one or more of other types of user equipment devices, or for content available both through a television and one or more of the other types of user equipment devices. The media guidance applications may be provided as on-line applications (i.e., provided on a web-site), or as stand-alone applications or clients on user equipment devices. Various devices and platforms that may implement media guidance applications are described in more detail below.

In some embodiments, the media guidance application may direct a target device to perform one or more media guidance application operations. As used herein, a "target device" refers to a user device that a user is attempting to control and/or that is otherwise the subject of commands issued by the user. In some embodiments, the target device may be the same or a separate device from the device used to monitor for first and/or second input types and/or the user device upon which the media guidance application is implemented.

In some embodiments, a media guidance application operation may relate to a social media activity such as publicly distributing information associated with a user. For example, the media guidance application may retrieve a list of entities such as friends (e.g., a social network buddy list), contacts (e.g., retrieved from a phone/text message/e-mail account associated with the user), and/or public services (e.g., hospitals, police departments, schools, etc.) with known associations to the user or the community of the user and generate for display information (e.g., a post content) on a social network.

As used herein, a "social network" refers to a platform that facilitates networking and/or social relations among people who, for example, share interests, activities, backgrounds, and/or real-life connections. In some cases, social networks may facilitate communication between multiple user devices (e.g., computers, televisions, smartphones, tablets, etc.) associated with different users by exchanging content from one device to another via a social media server. As used herein, a "social media server" refers to a computer server that facilitates a social network. For example, a social media server owned/operated/used by a social media provider may make content (e.g., status updates, microblog posts, images, graphic messages, etc.) associated with a first user accessible to a second user that is within the same social network as the first user. In such cases, classes of entities may correspond to the level of access and/or the amount or type of content associated with a first user that is accessible to a second user.

In some embodiments, the media guidance application may receive inputs to perform one or more media guidance application operations through a user input interface. As referred to herein, "an input" refers to any communication, request, and/or command to perform an action related to a media guidance application operation. In some embodiments, an input may be issued by a user. In some embodiments, inputs may correspond to particular types and/or categories (e.g., voice controls, motion controls, brain activity controls, etc.) and may be associated with a particular user input interface.

As used herein, a "user input interface" refers to any interface through which the media guidance application may receive inputs from a user. User input interfaces may be any suitable user interface, such as a remote control, mouse, trackball, keypad, keyboard, touch screen, touchpad, stylus input, joystick, voice recognition interface, motion recognition interface, brain activity monitoring interface, eye-tracking interface, or any other user input interface.

In some embodiments, a user input interface may include one of more specialized components for receiving, distinguishing between, cataloguing, and/or otherwise processing inputs of a particular type. For example, a user input interface configured to process voice controls may include one or more components for performing speech recognition. For example, in some embodiments, the media guidance application may include techniques, components, and/or algorithms, including, but not limited to, Hidden Markov Models, dynamic time warping, and/or neural networks to translate spoken words into text and/or processing audio data.

Furthermore, in some embodiments, the media guidance application may monitor for and/or distinguish between different characteristics of vocalizations, including, but not limited to, accents, pronunciations, articulations, roughnesses, nasalities, pitches, volumes, and speeds. The media guidance application may further store the various characteristics in one or more user profiles in which each user profile is associated with a user. The media guidance application may then access the user profile associated with a user when receiving commands in order to interpret and execute the commands with greater precision and/or in order to identify a user.

For example, the media guidance application may calibrate a user profile to accept commands in a particular accent. Moreover, the media guidance application may identify a user in response to detecting a particular accent (associated with the user) in a received command. Furthermore, the media guidance application may continuously or periodically recalibrate the user profile of the user to include the most recent and/or most accurate measurements of a characteristic. For example, the media guidance application may quantify the accent of a particular user using any technique that distinguishes the accent of that particular user from other users (e.g., associating the accent of the user with a particular value). During recalibration, the media guidance application may modify the quantification to reflect the current accent of the user.

Alternatively or additionally, the user input interface may be configured to process motion controls and include one or more components for monitoring and detecting a change in position of an object (e.g., a user) relative to its surroundings or the change in the surroundings relative to an object. User input interfaces configured to process motion controls may include, but are not limited to, infrared, optical, radio frequency energy, audio, vibration, and/or magnetic sensors.

For example, the media guidance application may calibrate a user profile to accept a command based on a particular gesture. Moreover, the media guidance application may identify a user in response to detecting a particular gesture (associated with the user) in a received command. Furthermore, the media guidance application may continuously or periodically recalibrate the user profile of the user to include the most recent and/or most accurate measurements of a characteristic. For example, the media guidance application may quantify the gesture of a particular user using any technique that distinguishes the gesture of that particular user from other users (e.g., associating the gesture of the user with a particular value). During recalibration, the media guidance application may modify the quantification to reflect the current gesture of the user.

Additionally or alternatively, the media guidance application may include object recognition capabilities. For example, a content recognition module, incorporated into, and/or accessible by, the media guidance application may use object recognition techniques such as edge detection, pattern recognition, including, but not limited to, self-learning systems (e.g., neural networks), optical character recognition, on-line character recognition (including, but not limited to, dynamic character recognition, real-time character recognition, intelligent character recognition), and/or any other suitable technique or method to determine whether or not a user performed a gesture, how long a user performed a gesture, how many gestures a user or group of users performed, the frequency of gestures performed by a user or a group of users, etc. For example, the media application may receive data in the form of a video of the user. The video may include a series of frames. For each frame of the video, the media application may use a content recognition module or algorithm to detect the people (e.g., the number of users in a viewing area) in each of the frames or series of frames and/or whether or not a gesture was performed by any of the users.

Additionally or alternatively, the user input interface may be configured to process controls based on the movements of the eyes of a user (e.g., to determine whether or not a user is looking at particular content) may include an eye contact detection component, which determines or receives a location upon which one or both of a user's eyes are focused. The location upon which a user's eyes are focused is referred to herein as the user's "gaze point." In some embodiments, the eye contact detection component may monitor one or both eyes of a user to identify a gaze point of one or more users. The eye contact detection component may additionally or alternatively determine whether one or both eyes of the user are focused on a location (e.g., another user).

Furthermore, the media guidance application may calibrate a user profile to accept a command based on a particular eye movement. Moreover, the media guidance application may identify a user in response to detecting a particular eye movement (associated with the user) in a received command. Furthermore, the media guidance application may continuously or periodically recalibrate the user profile of the user to include the most recent and/or most accurate measurements of a characteristic. For example, the media guidance application may quantify the eye movement of a particular user using any technique that distinguishes the eye movement of that particular user from other users (e.g., associating the eye movement of the user with a particular value). During recalibration, the media guidance application may modify the quantification to reflect the current eye movement of the user.

Alternatively or additionally, the user input interface may be configured to process controls based on brain activity and/or other biometric activity of the user and may include components to monitor and distinguish between the brain activity and/or biometric activity of a user. For example, in some embodiments, the media guidance application may monitor for specific biometric measurements about a user. Furthermore, a specific biometric measurement may be mapped by the media guidance application to the performance of a particular media guidance application operation. For example, in response to receiving biometric data about a user, the media guidance application may perform one or more media guidance application operations. As used herein, "biometric measurement" refers to distinctive, measurable characteristics used to label and describe the psychological or physiological condition of a user.

For example, biometric measurements that may be received, managed, monitored, and/or shared by a media guidance application may include psychological characteristics related to the level of concentration, emotional state, mood, and/or pattern of behavior of a person, including but not limited to typing rhythm, gait, frequency of social interactions, voice tones, etc., or may include physiological characteristics related to the status and/or shape of the body such as height, weight, medical condition(s), heart rate, blood pressure, fingerprint, body mass index, glucose level, face description, DNA, palm print, hand geometry, iris, retina, odor/scent, and/or any other mechanical, physical, and biochemical functions of a user, his/her organs, and the cells of which they are composed.

In some embodiments, the media guidance application may determine a psychological or physiological condition of a user based on one or more biometric measurements, and use that determination to trigger the performance of a media guidance application operation. For example, the media guidance application may determine the current mood of a user based on the heart rate, drowsiness level, or current brain activity of the user. In another example, the media guidance application may determine the level of attention of a user based on current brain activity, eye contact, etc. Systems and methods for determining moods, levels of attention, and other characteristics of a user based on brain activity and/or other biometric measurements are discussed in greater detail in connection with Klappert et al., U.S. patent application Ser. No. 14/038,158, filed Sep. 26, 2013; Klappert et al., U.S. patent application Ser. No. 14/038,046, filed Sep. 26, 2013; Klappert et al., U.S. patent application Ser. No. 14/038,171, filed Sep. 26, 2013; Klappert et al., U.S. patent application Ser. No. 14/038,257, filed Sep. 26, 2013; Klappert et al., U.S. patent application Ser. No. 14/037,984, filed Sep. 26, 2013; and Klappert et al., U.S. patent application Ser. No. 14/038,044, filed Sep. 26, 2013, which are hereby incorporated by reference herein in their entireties.

In some embodiments, monitoring for biometric data may including monitoring the brain activity of a user. For example, a characteristic of brain activity may be mapped such that detection of such a characteristic triggers a particular media guidance application operation. For example, the media guidance application may monitor the user to determine whether or not a specific brain state such as the user obtaining a particular mood, a particular level of concentration, a brain activity frequency range above a threshold level, or a particular amplitude with any one frequency band, etc., is occurring. If such a brain state is detected, the media guidance application may instruct a target device to perform a particular media guidance application operation that was mapped to the detected brain state.

As referred to herein, a "brain state" refers to a quantitative or qualitative assessment of brain activity. For example, a qualitative assessment of brain activity may include the mood, level of anxiety, level of attentiveness, level of comprehension, level of proficiency associated with one or more functions (e.g., reading text on a screen, hearing audio, etc.) of a user, and/or a combination thereof associated with the brain activity of the user. A quantitative assessment of a brain state may include whether or not brain activity meets a particular threshold range of brain activity, the current frequency range of voltage fluctuations in the brain, electrical activity of muscles near the brain at rest and during contraction, etc.

As referred to herein, a "threshold range" for brain activity refers to a frequency range and/or amplitude of brain activity that defines the boundaries of a brain state. For example, a threshold range may be defined as a particular frequency range (in Hz) associated with a brain activity of a user, may be defined as frequency bands associated with brain activity of a user, and/or may be defined according to any other measurement that describes the current, preferred, past, and/or future brain activity of a user. In some embodiments, a threshold range may account for any transient variations and amplitudes in brain state. For example, a threshold range may be defined as an average amplitude, frequency, frequency range, and/or frequency band over a particular period of time.

In addition, a threshold range may refer to a composite range that includes one or more amplitudes and/or frequencies associated with one or more waves. For example, in some embodiments, a particular brain state may correspond to brain activity corresponding to theta bands with a first amplitude and delta bands at a second amplitude.

It should also be noted that in some embodiments, a threshold range may itself include one or more threshold ranges. For example, a threshold range associated with one brain state (e.g., a user being awake) may itself include numerous other threshold ranges (e.g., a mood of the user, an attentiveness level of the user, etc.). Furthermore, in some embodiments, threshold ranges may refer to other types of inputs (e.g., voice controls, motion controls, etc.), in which case the boundaries of the threshold range may correspond to particular measurements and/or characteristics associated with the respective type of input.

Brain states may be identified by a user device (e.g., upon which a media guidance application is implemented) that incorporates and/or has access to a device for monitoring brain waves (e.g., an EEG, EMG, and/or any other device discussed herein). The media guidance application may monitor the brain activity (e.g., brain waves) of a user and determine multiple brain states of the user based on the brain activity. For example, the different user input types may each correspond to a particular brain state.

For example, whether or not a user currently has a first brain state (e.g., whether or not a user has a particular level of concentration) may indicate whether or not a first function (as mapped to a first input type to be associated with the first brain state) is triggered. Likewise, whether or not a user currently has a second brain state (e.g., whether or not a user has a delta band with a 200 microvolt amplitude) may indicate whether or not a second function (as mapped to the first input type to be associated with the second brain state) is triggered.

For example, the media guidance application may indicate that a first brain state corresponds to a particular frequency range of voltage fluctuations in the brain, electrical activity of muscles near the brain at rest and during contraction, and/or threshold range, and that a second brain state corresponds to a different frequency range of voltage fluctuations in the brain, electrical activity of muscles near the brain at rest and during contraction, and/or threshold range. If the user currently has a brain state corresponding to the first brain state, then a function associated with a media guidance application operation (e.g., changing a channel) is triggered. If the user currently has a brain state corresponding to the second brain state, then a function associated with a different media guidance application operation (e.g., increasing volume of a display device) is triggered. If the user currently has a brain state corresponding to both the first and the second brain state, then both functions are triggered. Likewise, if the user currently has a brain state corresponding to neither the first nor the second brain state, then neither function is triggered.

In some embodiments, the media guidance application may incorporate and/or have access to an electroencephalogram unit ("EEG"). An EEG measures electrical activity associated with a brain of a user. For example, an EEG may measure voltage fluctuations and/or the frequency or frequency range of voltage fluctuations generated by the brain of a user. For example, an EEG may describe rhythmic brain activity. Rhythmic activity (e.g., activity associated with neural oscillation) also known as brain waves may be described in terms of frequency bands or frequency ranges. For example, a delta band includes a frequency range of up to about 4 Hz with a typical amplitude of 20-200 microvolts. Delta bands are, in some circumstances, associated with a sleeping state of a user. Theta bands include a frequency range of 4 to 8 Hz with a typical amplitude of 10 microvolts. Theta bands are, in some circumstances, associated with drowsiness. Alpha bands include a frequency range of 8 to 13 Hz with a typical amplitude of 20-200 microvolts. Alpha bands are, in some circumstances, associated with a relaxed state and/or the blinking of a user's eyes. Beta bands include frequencies of 13 to 30 Hz with a typical amplitude of 5-10 microvolts. Beta bands are, in some circumstances, associated with alertness, concentration, and/or anxiety. Gamma bands include a frequency range of 30 to 100 Hz and may have various amplitudes. Gamma bands are, in some circumstances, associated with combinations of senses of a user (e.g., sight, smell, sound, touch, taste) and/or short-term memory. Frequency bands and frequency ranges as well as the symmetry of these bands and ranges across the brain of a user are also associated with various moods, which is discussed in detail in Rybak, "Frontal Alpha Power Asymmetry in Aggressive Children and Adolescents With Mood and Disruptive Behavior Disorders," Clinical EEL and Neuroscience, Vol. 3, 2006, which is hereby incorporated by reference herein in its entirety.

In some embodiments, the user device incorporates and/or has access to an electromyogram unit ("EMG"). An EMG measures the electrical activity of muscles at rest and during contraction. The use of EMG and EEG for providing biofeedback is discussed in detail in Frank et al., "Biofeedback in medicine: who, when, why and how?" Ment. Health Fam. Med., June 2010, and Wartena et al., U.S. Patent Application Publication No. 2012/0029322, filed Mar. 24, 2010, which are hereby incorporated by reference herein in their entireties. In some embodiments, the user device may include additional components for detecting brain activity, moods, and attentiveness of a user as discussed in detail in Lee et al., U.S. Pat. No. 8,332,883, issued Dec. 11, 2012, and Bill, U.S. Pat. No. 8,373,768, issued Feb. 12, 2013, which are hereby incorporated by reference herein in their entireties.

Furthermore, the media guidance application may calibrate a user profile to accept a command based on particular brain activity. Moreover, the media guidance application may identify a user in response to detecting the particular brain activity (associated with the user) in a received command. Furthermore, the media guidance application may continuously or periodically recalibrate the user profile of the user to include the most recent and/or most accurate measurements of a characteristic. For example, the media guidance application may quantify the brain activity of a particular user using any technique that distinguishes the brain activity of that particular user from other users (e.g., associating the brain activity of the user with a particular value). During recalibration, the media guidance application may modify the quantification to reflect the current brain activity of the user.

In some embodiments, the media guidance application may maintain calibrations for the various inputs (e.g., voice controls, motion controls, brain activity controls, etc.) that are received. For example, the media guidance application may periodically recalibrate the input to include the precision at which the media guidance application accepts commands. For example, a lack of precision may results in the lack of detection of a command when the command is issued from the user and/or the detection of the command even though the command was not used from the user.

To increase precision, the media guidance application may calibrate the measurements of commands (whether based on voice controls, motion controls, brain activity, etc.) that trigger a particular media guidance application operation to the measurements of commands that the user issues when the user wishes to trigger the command. Furthermore, the media guidance application may recalibrate continuously or periodically (e.g., accordingly to a predetermined schedule or rate).

In some embodiments, the media guidance application may recalibrate a user profile based on the age of a user as some types of inputs (and the calibrations of those inputs) may be affected by the age of a user. For example, as a user ages, the voice of the user may change. For example, during puberty, the pitch of the voice of a user may lower. Likewise, during a user's elderly years, the speed at which voice commands are issued may drop. In another example, as the user ages from a child to an adult, the coordination at which a user can issue motion controls may increase. However, during a user's elderly years, the coordination at which a user can issue motion controls may decrease. In another example, as a user ages, the development of the brain may cause changes to the brain activity generated by a user.

In each case, the media guidance may recalibrate the user profile to account for such changes. For example, the media guidance application may adjust the rate at which the user profile is recalibrated and/or the media guidance application may adjust how the user profile is recalibrated. For example, the media guidance application may access a database that indicates particular rates at which a user profile (or information therein) should be recalibrated. Likewise, the database, or a different database, may additionally or alternatively indicate how the user profile (or information therein) should be recalibrated.

For example, the media guidance application may cross-reference the current age of a user (e.g., twelve) with a database listing information about recalibrating user profiles for a given age. The media guidance application may input the age of the user (e.g., twelve). The database may filter the listing and output information about recalibrating user profiles for the inputted age (e.g., twelve). The media guidance may additionally or alternatively input the type of input (e.g., voice control). The database may filter (or may further filter) the outputted information about recalibrating user profiles based on the type of input.

For example, the information may indicate that user profiles associated with a user of the age of twelve should have voice controls recalibrated every two weeks (e.g., the onset of puberty may rapidly effect the precision of the calibration of the voice controls). Additionally or alternatively, the information may indicate that the controls should specifically have the pitch associated with the voice controls recalibrated (e.g., the onset of puberty may have more heavily affected the pitch of the voice of the user). Additionally or alternatively, the media guidance application may indicate a degree to which the pitch (or any characteristic of the input) should be recalibrated. For example, the media guidance application may indicate a specific amount that a current value associated with pitch should be recalibrated.

Additionally or alternatively, the media guidance application may query the user seeking the recalibration. For example, the media guidance application may determine whether or not a recalibration is needed (e.g., based on the recalibration rate). The media guidance application may then, additionally or alternatively, determine a particular characteristic of the input that needs to be recalibrated (e.g., pitch). The media guidance application may then query the user to obtain measurements for the characteristic that needs to be recalibrated.

For example, if the media guidance application is recalibrating voice controls, the media guidance application may request the user issue specific commands. The media guidance application may then recalibrate the user profile associated with the user based on the characteristics of the issued commands. For example, if the pitch of the voice controls is being recalibrated, the media guidance application may detect and measure the pitch of the issued commands. The detected measurements may then be used to establish the threshold range of the pitch of the user profile associated with the user. Thus, the user profile may be recalibrated such that the pitch of any future commands issued by the user is compared to the threshold range of the detected measurements.

In another example, if the media guidance application is recalibrating motion controls, the media guidance application may request the user issue specific gestures. The media guidance application may then recalibrate the user profile associated with the user based on the characteristics of the issued gestures. For example, if the speed of the motion controls is being recalibrated, the media guidance application may detect and measure the speed of the issued gestures. The detected measurements may then be used to establish the threshold range of the speed of gestures in the user profile associated with the user. Thus, the user profile may be recalibrated such that the speed of any future gestures issued by the user is compared to the threshold range of the detected measurements.

In another example, if the media guidance application is recalibrating controls based on brain activity, the media guidance application may use similar techniques to recalibrate the user profile. For example, the media guidance application may receive information from the user, in which the user describes and/or rates current brain states of the user. For example, during calibration, the media guidance application may detect a brain state and ask the user to describe the brain (e.g., designate the state as associated with a particular media guidance application operation). The current brain state of the user (e.g., the current threshold range) will then be designated as corresponding to the particular media guidance application operation. Additionally or alternatively, the media guidance application may receive instructions designating a particular brain state as corresponding to a particular media guidance application operation. For example, the media guidance application may retrieve/receive instructions that indicate that a threshold range of 8 to 10 Hz indicates that the particular user is performing a particular fast-access playback operation. Additionally, the media guidance application may retrieve/receive instructions that indicate that a threshold range of 10 to 13 Hz indicates that the particular user is performing a different fast-access playback operation. In another example, if the average amplitude of a threshold range is 50 microvolts and an average frequency range is 7 Hz, the media guidance application may determine that the threshold range indicates that a user is powering-off a target device.

Figure 2:
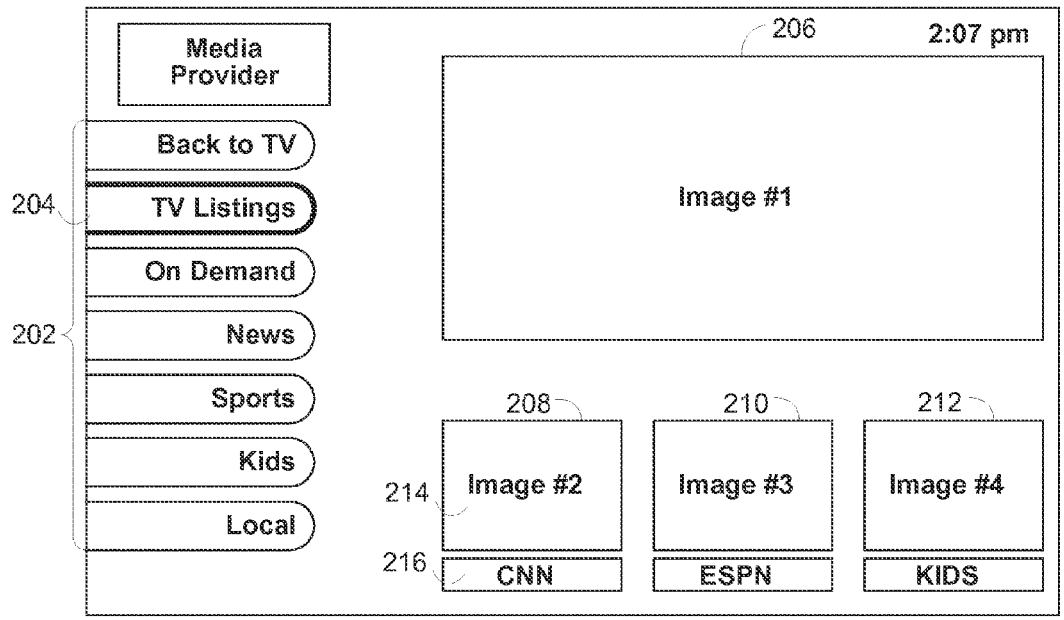
FIG. 2 shows another illustrative example of a display screen generated by a media guidance application in accordance with some embodiments of the disclosure.

FIGS. 1-2 show illustrative display screens that may be used to provide media guidance data. The display screens shown in FIGS. 1-2 may be implemented on any suitable user equipment device or platform. While the displays of FIGS. 1-2 are illustrated as full screen displays, they may also be fully or partially overlaid over content being displayed. A user may indicate a desire to access content information by selecting a selectable option provided in a display screen (e.g., a menu option, a listings option, an icon, a hyperlink, etc.) or pressing a dedicated button (e.g., a GUIDE button) on a remote control or other user input interface or device. In response to the user's indication, the media guidance application may provide a display screen with media guidance data organized in one of several ways, such as by time and channel in a grid, by time, by channel, by source, by content type, by category (e.g., movies, sports, news, children, or other categories of programming), or other predefined, user-defined, or other organization criteria.

FIG. 1 shows illustrative grid of a program listings display 100 arranged by time and channel that also enables access to different types of content in a single display. Display 100 may include grid 102 with: (1) a column of channel/content type identifiers 104, where each channel/content type identifier (which is a cell in the column) identifies a different channel or content type available; and (2) a row of time identifiers 106, where each time identifier (which is a cell in the row) identifies a time block of programming. Grid 102 also includes cells of program listings, such as program listing 108, where each listing provides the title of the program provided on the listing's associated channel and time. With a user input device, a user can select program listings by moving highlight region 110. Information relating to the program listing selected by highlight region 110 may be provided in program information region 112. Region 112 may include, for example, the program title, the program description, the time the program is provided (if applicable), the channel the program is on (if applicable), the program's rating, and other desired information.

In addition to providing access to linear programming (e.g., content that is scheduled to be transmitted to a plurality of user equipment devices at a predetermined time and is provided according to a schedule), the media guidance application also provides access to non-linear programming (e.g., content accessible to a user equipment device at any time and is not provided according to a schedule). Non-linear programming may include content from different content sources including on-demand content (e.g., VOD), Internet content (e.g., streaming media, downloadable media, etc.), locally stored content (e.g., content stored on any user equipment device described above or other storage device), or other time-independent content. On-demand content may include movies or any other content provided by a particular content provider (e.g., HBO On Demand providing "The Sopranos" and "Curb Your Enthusiasm"). HBO ON DEMAND is a service mark owned by Time Warner Company L.P. et al. and THE SOPRANOS and CURB YOUR ENTHUSIASM are trademarks owned by the Home Box Office, Inc. Internet content may include web events, such as a chat session or Webcast, or content available on-demand as streaming content or downloadable content through an Internet web site or other Internet access (e.g. FTP).

Grid 102 may provide media guidance data for non-linear programming including on-demand listing 114, recorded content listing 116, and Internet content listing 118. A display combining media guidance data for content from different types of content sources is sometimes referred to as a "mixed-media" display. Various permutations of the types of media guidance data that may be displayed that are different than display 100 may be based on user selection or guidance application definition (e.g., a display of only recorded and broadcast listings, only on-demand and broadcast listings, etc.). As illustrated, listings 114, 116, and 118 are shown as spanning the entire time block displayed in grid 102 to indicate that selection of these listings may provide access to a display dedicated to on-demand listings, recorded listings, or Internet listings, respectively. In some embodiments, listings for these content types may be included directly in grid 102. Additional media guidance data may be displayed in response to the user selecting one of the navigational icons 120. (Pressing an arrow key on a user input device may affect the display in a similar manner as selecting navigational icons 120.)

Display 100 may also include video region 122, advertisement 124, and options region 126. Video region 122 may allow the user to view and/or preview programs that are currently available, will be available, or were available to the user. The content of video region 122 may correspond to, or be independent from, one of the listings displayed in grid 102. Grid displays including a video region are sometimes referred to as picture-in-guide (PIG) displays. PIG displays and their functionalities are described in greater detail in Satterfield et al. U.S. Pat. No. 6,564,378, issued May 13, 2003 and Yuen et al. U.S. Pat. No. 6,239,794, issued May 29, 2001, which are hereby incorporated by reference herein in their entireties. PIG displays may be included in other media guidance application display screens of the embodiments described herein.

Advertisement 124 may provide an advertisement for content that, depending on a viewer's access rights (e.g., for subscription programming), is currently available for viewing, will be available for viewing in the future, or may never become available for viewing, and may correspond to or be unrelated to one or more of the content listings in grid 102. Advertisement 124 may also be for products or services related or unrelated to the content displayed in grid 102. Advertisement 124 may be selectable and provide further information about content, provide information about a product or a service, enable purchasing of content, a product, or a service, provide content relating to the advertisement, etc. Advertisement 124 may be targeted based on a user's profile/preferences, monitored user activity, the type of display provided, or on other suitable targeted advertisement bases.

While advertisement 124 is shown as rectangular or banner shaped, advertisements may be provided in any suitable size, shape, and location in a guidance application display. For example, advertisement 124 may be provided as a rectangular shape that is horizontally adjacent to grid 102. This is sometimes referred to as a panel advertisement. In addition, advertisements may be overlaid over content or a guidance application display or embedded within a display. Advertisements may also include text, images, rotating images, video clips, or other types of content described above. Advertisements may be stored in a user equipment device having a guidance application, in a database connected to the user equipment, in a remote location (including streaming media servers), or on other storage means, or a combination of these locations. Providing advertisements in a media guidance application is discussed in greater detail in, for example, Knudson et al., U.S. Patent Application Publication No. 2003/0110499, filed Jan. 17, 2003; Ward, III et al. U.S. Pat. No. 6,756,997, issued Jun. 29, 2004; and Schein et al. U.S. Pat. No. 6,388,714, issued May 14, 2002, which are hereby incorporated by reference herein in their entireties. It will be appreciated that advertisements may be included in other media guidance application display screens of the embodiments described herein.

Options region 126 may allow the user to access different types of content, media guidance application displays, and/or media guidance application features. Options region 126 may be part of display 100 (and other display screens described herein), or may be invoked by a user by selecting an on-screen option or pressing a dedicated or assignable button on a user input device. The selectable options within options region 126 may concern features related to program listings in grid 102 or may include options available from a main menu display. Features related to program listings may include searching for other air times or ways of receiving a program, recording a program, enabling series recording of a program, setting program and/or channel as a favorite, purchasing a program, or other features. Options available from a main menu display may include search options, VOD options, parental control options, Internet options, cloud-based options, device synchronization options, second screen device options, options to access various types of media guidance data displays, options to subscribe to a premium service, options to edit a user's profile, options to access a browse overlay, or other options.

The media guidance application may be personalized based on a user's preferences. A personalized media guidance application allows a user to customize displays and features to create a personalized "experience" with the media guidance application. This personalized experience may be created by allowing a user to input these customizations and/or by the media guidance application monitoring user activity to determine various user preferences. Users may access their personalized guidance application by logging in or otherwise identifying themselves to the guidance application. Customization of the media guidance application may be made in accordance with a user profile. The customizations may include varying presentation schemes (e.g., color scheme of displays, font size of text, etc.), aspects of content listings displayed (e.g., only HDTV or only 3D programming, user-specified broadcast channels based on favorite channel selections, re-ordering the display of channels, recommended content, etc.), desired recording features (e.g., recording or series recordings for particular users, recording quality, etc.), parental control settings, customized presentation of Internet content (e.g., presentation of social media content, e-mail, electronically delivered articles, etc.) and other desired customizations.

The media guidance application may allow a user to provide user profile information or may automatically compile user profile information. The media guidance application may, for example, monitor the content the user accesses and/or other interactions the user may have with the guidance application. Additionally, the media guidance application may obtain all or part of other user profiles that are related to a particular user (e.g., from other web sites on the Internet the user accesses, such as www.allrovi.com, from other media guidance applications the user accesses, from other interactive applications the user accesses, from another user equipment device of the user, etc.), and/or obtain information about the user from other sources that the media guidance application may access. As a result, a user can be provided with a unified guidance application experience across the user's different user equipment devices. This type of user experience is described in greater detail below in connection with FIG. 4. Additional personalized media guidance application features are described in greater detail in Ellis et al., U.S. Patent Application Publication No. 2005/0251827, filed Jul. 11, 2005, Boyer et al., U.S. Pat. No. 7,165,098, issued Jan. 16, 2007, and Ellis et al., U.S. Patent Application Publication No. 2002/0174430, filed Feb. 21, 2002, which are hereby incorporated by reference herein in their entireties.

Another display arrangement for providing media guidance is shown in FIG. 2. Video mosaic display 200 includes selectable options 202 for content information organized based on content type, genre, and/or other organization criteria. In display 200, television listings option 204 is selected, thus providing listings 206, 208, 210, and 212 as broadcast program listings. In display 200 the listings may provide graphical images including cover art, still images from the content, video clip previews, live video from the content, or other types of content that indicate to a user the content being described by the media guidance data in the listing. Each of the graphical listings may also be accompanied by text to provide further information about the content associated with the listing. For example, listing 208 may include more than one portion, including media portion 214 and text portion 216. Media portion 214 and/or text portion 216 may be selectable to view content in full-screen or to view information related to the content displayed in media portion 214 (e.g., to view listings for the channel that the video is displayed on).

The listings in display 200 are of different sizes (i.e., listing 206 is larger than listings 208, 210, and 212), but if desired, all the listings may be the same size. Listings may be of different sizes or graphically accentuated to indicate degrees of interest to the user or to emphasize certain content, as desired by the content provider or based on user preferences. Various systems and methods for graphically accentuating content listings are discussed in, for example, Yates, U.S. Patent Application Publication No. 2010/0153885, filed Dec. 29, 2005, which is hereby incorporated by reference herein in its entirety.

Figure 3:
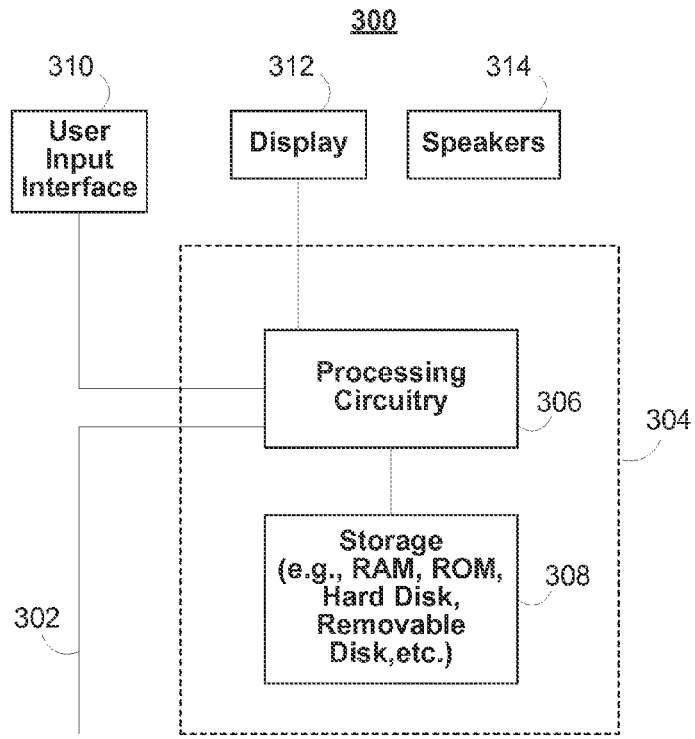
FIG. 3 is a block diagram of an illustrative user equipment device in accordance with some embodiments of the disclosure.

Users may access content and the media guidance application (and its display screens described above and below) from one or more of their user equipment devices. FIG. 3 shows a generalized embodiment of illustrative user equipment device 300. More specific implementations of user equipment devices are discussed below in connection with FIG. 4. User equipment device 300 may receive content and data via input/output (hereinafter "I/O") path 302. I/O path 302 may provide content (e.g., broadcast programming, on-demand programming, Internet content, content available over a local area network (LAN) or wide area network (WAN), and/or other content) and data to control circuitry 304, which includes processing circuitry 306 and storage 308. Control circuitry 304 may be used to send and receive commands, requests, and other suitable data using I/O path 302. I/O path 302 may connect control circuitry 304 (and specifically processing circuitry 306) to one or more communications paths (described below). I/O functions may be provided by one or more of these communications paths, but are shown as a single path in FIG. 3 to avoid overcomplicating the drawing.

Control circuitry 304 may be based on any suitable processing circuitry such as processing circuitry 306. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 304 executes instructions for a media guidance application stored in memory (i.e., storage 308). Specifically, control circuitry 304 may be instructed by the media guidance application to perform the functions discussed above and below. For example, the media guidance application may provide instructions to control circuitry 304 to generate the media guidance displays. In some implementations, any action performed by control circuitry 304 may be based on instructions received from the media guidance application.

In client-server based embodiments, control circuitry 304 may include communications circuitry suitable for communicating with a guidance application server or other networks or servers. The instructions for carrying out the above mentioned functionality may be stored on the guidance application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths (which is described in more detail in connection with FIG. 4). In addition, communications circuitry may include circuitry that enables peer-to-peer communication of user equipment devices, or communication of user equipment devices in locations remote from each other (described in more detail below).

Memory may be an electronic storage device provided as storage 308 that is part of control circuitry 304. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 308 may be used to store various types of content described herein as well as media guidance data described above. Nonvolatile memory may also be used (e.g., to launch a boot-up routine and other instructions). Cloud-based storage, described in relation to FIG. 4, may be used to supplement storage 308 or instead of storage 308.

Control circuitry 304 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 304 may also include scaler circuitry for upconverting and downconverting content into the preferred output format of the user equipment 300. Circuitry 304 may also include digital-to-analog converter circuitry and analog-to-digital converter circuitry for converting between digital and analog signals. The tuning and encoding circuitry may be used by the user equipment device to receive and to display, to play, or to record content. The tuning and encoding circuitry may also be used to receive guidance data. The circuitry described herein, including for example, the tuning, video generating, encoding, decoding, encrypting, decrypting, scaler, and analog/digital circuitry, may be implemented using software running on one or more general purpose or specialized processors. Multiple tuners may be provided to handle simultaneous tuning functions (e.g., watch and record functions, picture-in-picture (PIP) functions, multiple-tuner recording, etc.). If storage 308 is provided as a separate device from user equipment 300, the tuning and encoding circuitry (including multiple tuners) may be associated with storage 308.

A user may send instructions to control circuitry 304 using user input interface 310. User input interface 310 may be any suitable user interface, such as a remote control, mouse, trackball, keypad, keyboard, touch screen, touchpad, stylus input, joystick, voice recognition interface, or other user input interfaces. Additionally, user input interface 310 may include various components (e.g., a video detection component, an audio detection component, object recognition module, etc.) as discussed above for user in processing and recalibrating inputs of various types.

Display 312 may be provided as a stand-alone device or integrated with other elements of user equipment device 300. For example, display 312 may be a touchscreen or touch-sensitive display. In such circumstances, user input interface 312 may be integrated with or combined with display 312. Display 312 may be one or more of a monitor, a television, a liquid crystal display (LCD) for a mobile device, amorphous silicon display, low temperature poly silicon display, electronic ink display, electrophoretic display, active matrix display, electro-wetting display, electrofluidic display, cathode ray tube display, light-emitting diode display, electroluminescent display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. In some embodiments, display 312 may be HDTV-capable. In some embodiments, display 312 may be a 3D display, and the interactive media guidance application and any suitable content may be displayed in 3D. A video card or graphics card may generate the output to the display 312. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 304. The video card may be integrated with the control circuitry 304. Speakers 314 may be provided as integrated with other elements of user equipment device 300 or may be stand-alone units. The audio component of videos and other content displayed on display 312 may be played through speakers 314. In some embodiments, the audio may be distributed to a receiver (not shown), which processes and outputs the audio via speakers 314.

The guidance application may be implemented using any suitable architecture. For example, it may be a stand-alone application wholly-implemented on user equipment device 300. In such an approach, instructions of the application are stored locally (e.g., in storage 308), and data for use by the application is downloaded on a periodic basis (e.g., from an out-of-band feed, from an Internet resource, or using another suitable approach). Control circuitry 304 may retrieve instructions of the application from storage 308 and process the instructions to generate any of the displays discussed herein. Based on the processed instructions, control circuitry 304 may determine what action to perform when input is received from input interface 310. For example, movement of a cursor on a display up/down may be indicated by the processed instructions when input interface 310 indicates that an up/down button was selected.

In some embodiments, the media guidance application is a client-server based application. Data for use by a thick or thin client implemented on user equipment device 300 is retrieved on-demand by issuing requests to a server remote to the user equipment device 300. In one example of a client-server based guidance application, control circuitry 304 runs a web browser that interprets web pages provided by a remote server. For example, the remote server may store the instructions for the application in a storage device. The remote server may process the stored instructions using circuitry (e.g., control circuitry 304) and generate the displays discussed above and below. The client device may receive the displays generated by the remote server and may display the content of the displays locally on equipment device 300. This way, the processing of the instructions is performed remotely by the server while the resulting displays are provided locally on equipment device 300. Equipment device 300 may receive inputs from the user via input interface 310 and transmit those inputs to the remote server for processing and generating the corresponding displays. For example, equipment device 300 may transmit a communication to the remote server indicating that an up/down button was selected via input interface 310. The remote server may process instructions in accordance with that input and generate a display of the application corresponding to the input (e.g., a display that moves a cursor up/down). The generated display is then transmitted to equipment device 300 for presentation to the user.

In some embodiments, the media guidance application is downloaded and interpreted or otherwise run by an interpreter or virtual machine (run by control circuitry 304). In some embodiments, the guidance application may be encoded in the ETV Binary Interchange Format (EBIF), received by control circuitry 304 as part of a suitable feed, and interpreted by a user agent running on control circuitry 304. For example, the guidance application may be an EBIF application. In some embodiments, the guidance application may be defined by a series of JAVA-based files that are received and run by a local virtual machine or other suitable middleware executed by control circuitry 304. In some of such embodiments (e.g., those employing MPEG-2 or other digital media encoding schemes), the guidance application may be, for example, encoded and transmitted in an MPEG-2 object carousel with the MPEG audio and video packets of a program.

Figure 4:
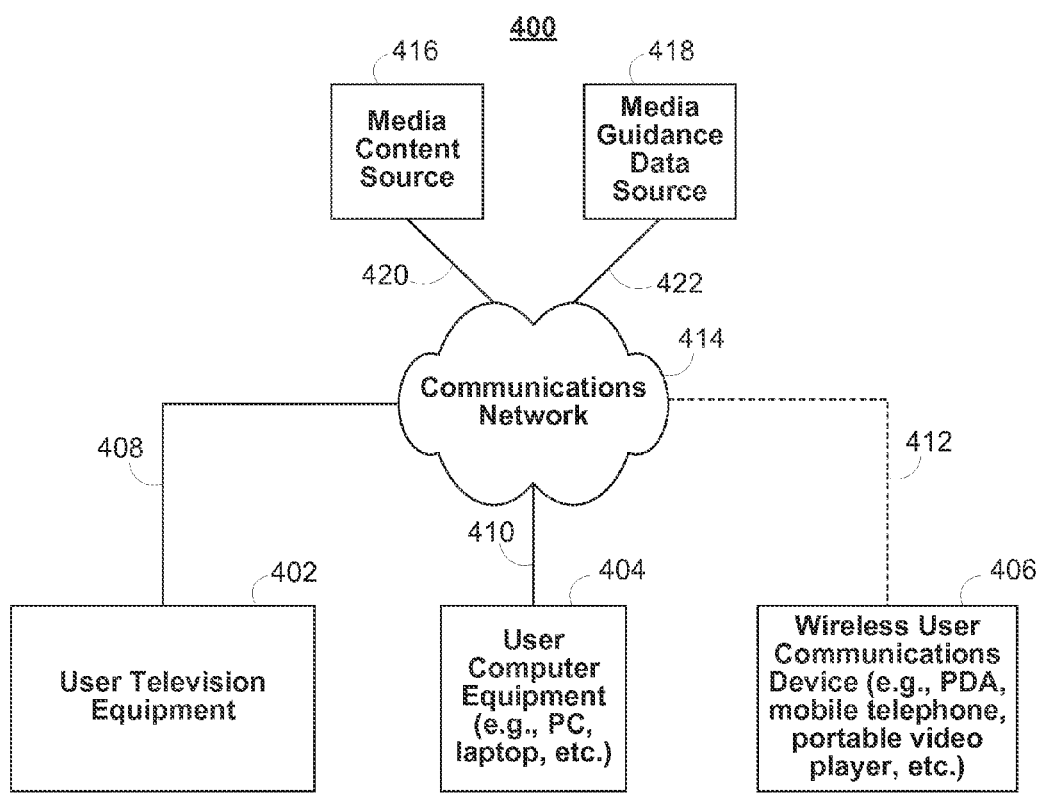
FIG. 4 is a block diagram of an illustrative media system in accordance with some embodiments of the disclosure.

User equipment device 300 of FIG. 3 can be implemented in system 400 of FIG. 4 as user television equipment 402, user computer equipment 404, wireless user communications device 406, or any other type of user equipment suitable for accessing content, such as a non-portable gaming machine. For simplicity, these devices may be referred to herein collectively as user equipment or user equipment devices, and may be substantially similar to user equipment devices described above. User equipment devices, on which a media guidance application may be implemented, may function as a standalone device or may be part of a network of devices. Various network configurations of devices may be implemented and are discussed in more detail below.

A user equipment device utilizing at least some of the system features described above in connection with FIG. 3 may not be classified solely as user television equipment 402, user computer equipment 404, or a wireless user communications device 406. For example, user television equipment 402 may, like some user computer equipment 404, be Internet-enabled allowing for access to Internet content, while user computer equipment 404 may, like some television equipment 402, include a tuner allowing for access to television programming. The media guidance application may have the same layout on various different types of user equipment or may be tailored to the display capabilities of the user equipment. For example, on user computer equipment 404, the guidance application may be provided as a web site accessed by a web browser. In another example, the guidance application may be scaled down for wireless user communications devices 406.

In system 400, there is typically more than one of each type of user equipment device but only one of each is shown in FIG. 4 to avoid overcomplicating the drawing. In addition, each user may utilize more than one type of user equipment device and also more than one of each type of user equipment device.

In some embodiments, a user equipment device (e.g., user television equipment 402, user computer equipment 404, wireless user communications device 406) may be referred to as a "second screen device." For example, a second screen device may supplement content presented on a first user equipment device. The content presented on the second screen device may be any suitable content that supplements the content presented on the first device. In some embodiments, the second screen device provides an interface for adjusting settings and display preferences of the first device. In some embodiments, the second screen device is configured for interacting with other second screen devices or for interacting with a social network. The second screen device can be located in the same room as the first device, a different room from the first device but in the same house or building, or in a different building from the first device.

The user may also set various settings to maintain consistent media guidance application settings across in-home devices and remote devices. Settings include those described herein, as well as channel and program favorites, programming preferences that the guidance application utilizes to make programming recommendations, display preferences, and other desirable guidance settings. For example, if a user sets a channel as a favorite on, for example, the web site www.allrovi.com on their personal computer at their office, the same channel would appear as a favorite on the user's in-home devices (e.g., user television equipment and user computer equipment) as well as the user's mobile devices, if desired. Therefore, changes made on one user equipment device can change the guidance experience on another user equipment device, regardless of whether they are the same or a different type of user equipment device. In addition, the changes made may be based on settings input by a user, as well as user activity monitored by the guidance application.

The user equipment devices may be coupled to communications network 414. Namely, user television equipment 402, user computer equipment 404, and wireless user communications device 406 are coupled to communications network 414 via communications paths 408, 410, and 412, respectively. Communications network 414 may be one or more networks including the Internet, a mobile phone network, mobile voice or data network (e.g., a 4G or LTE network), cable network, public switched telephone network, or other types of communications network or combinations of communications networks. Paths 408, 410, and 412 may separately or together include one or more communications paths, such as, a satellite path, a fiber-optic path, a cable path, a path that supports Internet communications (e.g., IPTV), free-space connections (e.g., for broadcast or other wireless signals), or any other suitable wired or wireless communications path or combination of such paths. Path 412 is drawn with dotted lines to indicate that in the exemplary embodiment shown in FIG. 4 it is a wireless path and paths 408 and 410 are drawn as solid lines to indicate they are wired paths (although these paths may be wireless paths, if desired). Communications with the user equipment devices may be provided by one or more of these communications paths, but are shown as a single path in FIG. 4 to avoid overcomplicating the drawing.

Although communications paths are not drawn between user equipment devices, these devices may communicate directly with each other via communication paths, such as those described above in connection with paths 408, 410, and 412, as well as other short-range point-to-point communication paths, such as USB cables, IEEE 1394 cables, wireless paths (e.g., Bluetooth, infrared, IEEE 802-11x, etc.), or other short-range communication via wired or wireless paths. BLUETOOTH is a certification mark owned by Bluetooth SIG, INC. The user equipment devices may also communicate with each other directly through an indirect path via communications network 414.

System 400 includes content source 416 and media guidance data source 418 coupled to communications network 414 via communication paths 420 and 422, respectively. Paths 420 and 422 may include any of the communication paths described above in connection with paths 408, 410, and 412. Communications with the content source 416 and media guidance data source 418 may be exchanged over one or more communications paths, but are shown as a single path in FIG. 4 to avoid overcomplicating the drawing. In addition, there may be more than one of each of content source 416 and media guidance data source 418, but only one of each is shown in FIG. 4 to avoid overcomplicating the drawing. (The different types of each of these sources are discussed below.) If desired, content source 416 and media guidance data source 418 may be integrated as one source device. Although communications between sources 416 and 418 with user equipment devices 402, 404, and 406 are shown as through communications network 414, in some embodiments, sources 416 and 418 may communicate directly with user equipment devices 402, 404, and 406 via communication paths (not shown) such as those described above in connection with paths 408, 410, and 412.

Content source 416 may include one or more types of content distribution equipment including a television distribution facility, cable system headend, satellite distribution facility, programming sources (e.g., television broadcasters, such as NBC, ABC, HBO, etc.), intermediate distribution facilities and/or servers, Internet providers, on-demand media servers, and other content providers. NBC is a trademark owned by the National Broadcasting Company, Inc., ABC is a trademark owned by the American Broadcasting Company, Inc., and HBO is a trademark owned by the Home Box Office, Inc. Content source 416 may be the originator of content (e.g., a television broadcaster, a Webcast provider, etc.) or may not be the originator of content (e.g., an on-demand content provider, an Internet provider of content of broadcast programs for downloading, etc.). Content source 416 may include cable sources, satellite providers, on-demand providers, Internet providers, over-the-top content providers, or other providers of content. Content source 416 may also include a remote media server used to store different types of content (including video content selected by a user), in a location remote from any of the user equipment devices. Systems and methods for remote storage of content, and providing remotely stored content to user equipment are discussed in greater detail in connection with Ellis et al., U.S. Pat. No. 7,761,892, issued Jul. 20, 2010, which is hereby incorporated by reference herein in its entirety.

Media guidance data source 418 may provide media guidance data, such as the media guidance data described above. Media guidance data may be provided to the user equipment devices using any suitable approach. In some embodiments, the guidance application may be a stand-alone interactive television program guide that receives program guide data via a data feed (e.g., a continuous feed or trickle feed). Program schedule data and other guidance data may be provided to the user equipment on a television channel sideband, using an in-band digital signal, using an out-of-band digital signal, or by any other suitable data transmission technique. Program schedule data and other media guidance data may be provided to user equipment on multiple analog or digital television channels.

In some embodiments, guidance data from media guidance data source 418 may be provided to users' equipment using a client-server approach. For example, a user equipment device may pull media guidance data from a server, or a server may push media guidance data to a user equipment device. In some embodiments, a guidance application client residing on the user's equipment may initiate sessions with source 418 to obtain guidance data when needed, e.g., when the guidance data is out of date or when the user equipment device receives a request from the user to receive data. Media guidance may be provided to the user equipment with any suitable frequency (e.g., continuously, daily, a user-specified period of time, a system-specified period of time, in response to a request from user equipment, etc.). Media guidance data source 418 may provide user equipment devices 402, 404, and 406 the media guidance application itself or software updates for the media guidance application.

In some embodiments, the media guidance data may include viewer data. For example, the viewer data may include current and/or historical user activity information (e.g., what content the user typically watches, what times of day the user watches content, whether the user interacts with a social network, at what times the user interacts with a social network to post information, what types of content the user typically watches (e.g., pay TV or free TV), mood, brain activity information, etc.). The media guidance data may also include subscription data. For example, the subscription data may identify to which sources or services a given user subscribes and/or to which sources or services the given user has previously subscribed but later terminated access (e.g., whether the user subscribes to premium channels, whether the user has added a premium level of services, whether the user has increased Internet speed). In some embodiments, the viewer data and/or the subscription data may identify patterns of a given user for a period of more than one year. The media guidance data may include a model (e.g., a survivor model) used for generating a score that indicates a likelihood a given user will terminate access to a service/source. For example, the media guidance application may process the viewer data with the subscription data using the model to generate a value or score that indicates a likelihood of whether the given user will terminate access to a particular service or source. In particular, a higher score may indicate a higher level of confidence that the user will terminate access to a particular service or source. Based on the score, the media guidance application may generate promotions and advertisements that entice the user to keep the particular service or source indicated by the score as one to which the user will likely terminate access.

Media guidance applications may be, for example, stand-alone applications implemented on user equipment devices. For example, the media guidance application may be implemented as software or a set of executable instructions which may be stored in storage 308, and executed by control circuitry 304 of a user equipment device 300. In some embodiments, media guidance applications may be client-server applications where only a client application resides on the user equipment device, and server application resides on a remote server. For example, media guidance applications may be implemented partially as a client application on control circuitry 304 of user equipment device 300 and partially on a remote server as a server application (e.g., media guidance data source 418) running on control circuitry of the remote server. When executed by control circuitry of the remote server (such as media guidance data source 418), the media guidance application may instruct the control circuitry to generate the guidance application displays and transmit the generated displays to the user equipment devices. The server application may instruct the control circuitry of the media guidance data source 418 to transmit data for storage on the user equipment. The client application may instruct control circuitry of the receiving user equipment to generate the guidance application displays.

Content and/or media guidance data delivered to user equipment devices 402, 404, and 406 may be over-the-top (OTT) content. OTT content delivery allows Internet-enabled user devices, including any user equipment device described above, to receive content that is transferred over the Internet, including any content described above, in addition to content received over cable or satellite connections. OTT content is delivered via an Internet connection provided by an Internet service provider (ISP), but a third party distributes the content. The ISP may not be responsible for the viewing abilities, copyrights, or redistribution of the content, and may only transfer IP packets provided by the OTT content provider. Examples of OTT content providers include YOUTUBE, NETFLIX, and HULU, which provide audio and video via IP packets. Youtube is a trademark owned by Google Inc., Netflix is a trademark owned by Netflix Inc., and Hulu is a trademark owned by Hulu, LLC. OTT content providers may additionally or alternatively provide media guidance data described above. In addition to content and/or media guidance data, providers of OTT content can distribute media guidance applications (e.g., web-based applications or cloud-based applications), or the content can be displayed by media guidance applications stored on the user equipment device.

Media guidance system 400 is intended to illustrate a number of approaches, or network configurations, by which user equipment devices and sources of content and guidance data may communicate with each other for the purpose of accessing content and providing media guidance. The embodiments described herein may be applied in any one or a subset of these approaches, or in a system employing other approaches for delivering content and providing media guidance. The following four approaches provide specific illustrations of the generalized example of FIG. 4.

In one approach, user equipment devices may communicate with each other within a home network. User equipment devices can communicate with each other directly via short-range point-to-point communication schemes described above, via indirect paths through a hub or other similar device provided on a home network, or via communications network 414. Each of the multiple individuals in a single home may operate different user equipment devices on the home network. As a result, it may be desirable for various media guidance information or settings to be communicated between the different user equipment devices. For example, it may be desirable for users to maintain consistent media guidance application settings on different user equipment devices within a home network, as described in greater detail in Ellis et al., U.S. patent application Ser. No. 11/179,410, filed Jul. 11, 2005. Different types of user equipment devices in a home network may also communicate with each other to transmit content. For example, a user may transmit content from user computer equipment to a portable video player or portable music player.

In a second approach, users may have multiple types of user equipment by which they access content and obtain media guidance. For example, some users may have home networks that are accessed by in-home and mobile devices. Users may control in-home devices via a media guidance application implemented on a remote device. For example, users may access an online media guidance application on a website via a personal computer at their office, or a mobile device such as a PDA or web-enabled mobile telephone. The user may set various settings (e.g., recordings, reminders, or other settings) on the online guidance application to control the user's in-home equipment. The online guide may control the user's equipment directly, or by communicating with a media guidance application on the user's in-home equipment. Various systems and methods for user equipment devices communicating, where the user equipment devices are in locations remote from each other, is discussed in, for example, Ellis et al., U.S. Pat. No. 8,046,801, issued Oct. 25, 2011, which is hereby incorporated by reference herein in its entirety.

In a third approach, users of user equipment devices inside and outside a home can use their media guidance application to communicate directly with content source 416 to access content. Specifically, within a home, users of user television equipment 402 and user computer equipment 404 may access the media guidance application to navigate among and locate desirable content. Users may also access the media guidance application outside of the home using wireless user communications devices 406 to navigate among and locate desirable content.

In a fourth approach, user equipment devices may operate in a cloud computing environment to access cloud services. In a cloud computing environment, various types of computing services for content sharing, storage or distribution (e.g., video sharing sites or social networking sites) are provided by a collection of network-accessible computing and storage resources, referred to as "the cloud." For example, the cloud can include a collection of server computing devices, which may be located centrally or at distributed locations, that provide cloud-based services to various types of users and devices connected via a network such as the Internet via communications network 414. These cloud resources may include one or more content sources 416 and one or more media guidance data sources 418. In addition or in the alternative, the remote computing sites may include other user equipment devices, such as user television equipment 402, user computer equipment 404, and wireless user communications device 406. For example, the other user equipment devices may provide access to a stored copy of a video or a streamed video. In such embodiments, user equipment devices may operate in a peer-to-peer manner without communicating with a central server.

The cloud provides access to services, such as content storage, content sharing, or social networking services, among other examples, as well as access to any content described above, for user equipment devices. Services can be provided in the cloud through cloud computing service providers, or through other providers of online services. For example, the cloud-based services can include a content storage service, a content sharing site, a social networking site, or other services via which user-sourced content is distributed for viewing by others on connected devices. These cloud-based services may allow a user equipment device to store content to the cloud and to receive content from the cloud rather than storing content locally and accessing locally-stored content.

A user may use various content capture devices, such as camcorders, digital cameras with video mode, audio recorders, mobile phones, and handheld computing devices, to record content. The user can upload content to a content storage service on the cloud either directly, for example, from user computer equipment 404 or wireless user communications device 406 having content capture feature. Alternatively, the user can first transfer the content to a user equipment device, such as user computer equipment 404. The user equipment device storing the content uploads the content to the cloud using a data transmission service on communications network 414. In some embodiments, the user equipment device itself is a cloud resource, and other user equipment devices can access the content directly from the user equipment device on which the user stored the content.

Cloud resources may be accessed by a user equipment device using, for example, a web browser, a media guidance application, a desktop application, a mobile application, and/or any combination of access applications of the same. The user equipment device may be a cloud client that relies on cloud computing for application delivery, or the user equipment device may have some functionality without access to cloud resources. For example, some applications running on the user equipment device may be cloud applications, i.e., applications delivered as a service over the Internet, while other applications may be stored and run on the user equipment device. In some embodiments, a user device may receive content from multiple cloud resources simultaneously. For example, a user device can stream audio from one cloud resource while downloading content from a second cloud resource. Or a user device can download content from multiple cloud resources for more efficient downloading. In some embodiments, user equipment devices can use cloud resources for processing operations such as the processing operations performed by processing circuitry described in relation to FIG. 3.

Figure 5:
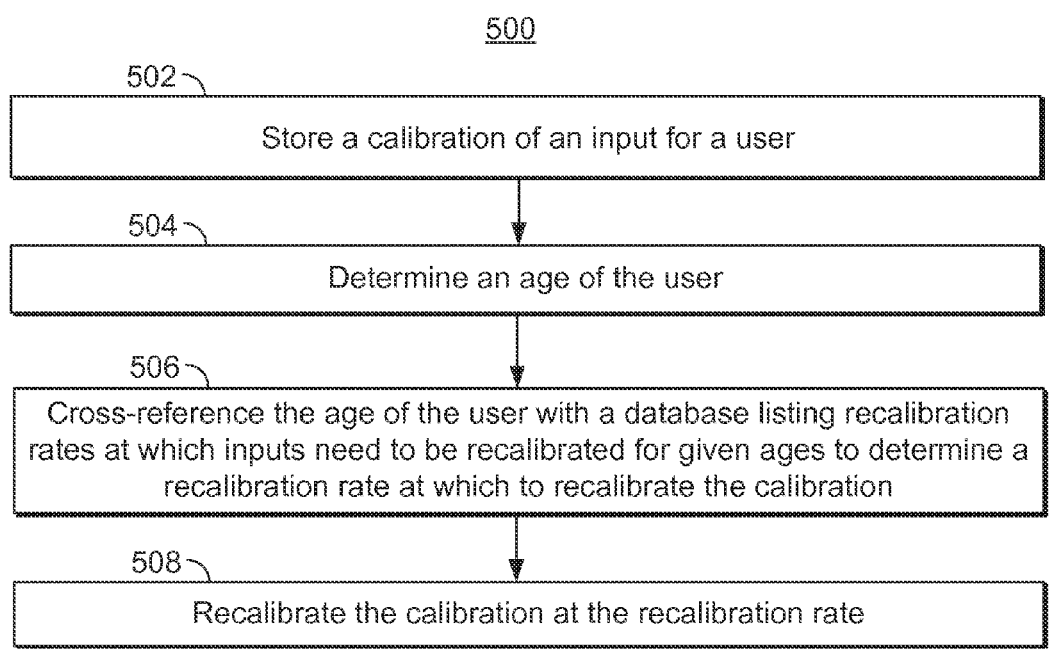
FIG. 5 is a flowchart of illustrative steps for determining a recalibration rate based on the age of a user in accordance with some embodiments of the disclosure.

FIG. 5 is a flowchart of illustrative steps for determining a recalibration rate based on the age of a user. It should be noted that process 500 or any step thereof could be performed on, or provided by, any of the devices shown in FIGS. 3-4. For example, process 500 may be executed by control circuitry 304 (FIG. 3) as instructed by a media guidance application implemented on user equipment 402, 404, and/or 406 (FIG. 4) in order to determine a recalibration rate based on the age of a user. In addition, one or more steps of process 500 may be incorporated into or combined with one or more steps of any other process or embodiment (e.g., as described in relation to FIGS. 6-8).

At step 502, the media guidance application stores (e.g., at storage circuitry 308 (FIG. 3)) a calibration of an input for a user. For example, the media guidance application may store a calibration for an input (e.g., for user input interface 310 (FIG. 3)) in a user profile (e.g., stored at storage circuitry 308 (FIG. 3) and/or any location accessible via communications network 414 (FIG. 4)) associated with a user. The calibration may indicate particular adjustments to data received from a user and/or instruments used to receive data from the user that may increase the precision at which inputs are received and/or processed.

At step 504, the media guidance application determines (e.g., using control circuitry 304 (FIG. 3)) an age of the user. For example, upon creating a user profile (e.g., stored at storage circuitry 308 (FIG. 3) and/or any location accessible via communications network 414 (FIG. 4)), the media guidance may record an initial age of the user (e.g., based on one or more user queries). For example, upon detecting a new user (e.g., a user not associated with a user profile), the media guidance application may create (e.g., via control circuitry 304 (FIG. 3)) a user profile associated with that user. In such cases, the media guidance application may obtain information about the user such as the name, age, birth date, and/or any other relevant data. The media guidance application then may continuously or periodically update (e.g., via control circuitry 304 (FIG. 3)) the age of the user in order to determine the current age of the user.

For example, the media guidance application may (e.g., in control circuitry 304 (FIG. 3)) incorporate and/or have access to a calendar and/or timekeeping function that may determine the current date. The media guidance application may compare (e.g., via control circuitry 304 (FIG. 3)) the previously listed age and/or birth date of the user (e.g., stored in the user profile) to the current date to determine a current age of the user. For example, a previously listed age may be replaced with a new calculated age (e.g., based on the birth date of the user and the current date) or may be appended by adding a length of time corresponding to the amount of time from the current time to the time when the listed age was last updated to the listed age.

At step 506, the media guidance application cross-references (e.g., using control circuitry 304 (FIG. 3)) the age of the user with a database (e.g., located at storage 308 (FIG. 3) and/or any location accessible via communications network 414 (FIG. 4)) listing recalibration rates at which inputs need to be recalibrated for given ages to determine a recalibration rate at which to recalibrate the calibration. For example, in response to determining that user is a particular age, the media guidance application may determine (e.g., via control circuitry 304 (FIG. 3)) the rate at which an input, user input interface, and/or user profile associated with a user of that particular age should be recalibrated.

For example, the media guidance application may determine (e.g., via control circuitry 304 (FIG. 3)) a length of time since a previous recalibration (e.g., as recorded at storage 308 (FIG. 3) and/or any location accessible via communications network 414 (FIG. 4)) and compare (e.g., via control circuitry 304 (FIG. 3)) the recalibration rate to the length of time to determine whether or not the calibration needs to be recalibrated. For example, the media guidance application may determine (e.g., via control circuitry 304 (FIG. 3)) that the recalibration rate should correspond to a recalibration after a particular length of time. The media guidance application may then determine whether or not the length of time from the current point in time to the point in time of the last recalibration (if any) is greater than or equal to the particular length of time. For example, if the recalibration rate indicates that the input should be recalibrated once every two weeks, the media guidance application may determine whether or not the input has been recalibrated within the last two weeks.

At step 508, the media guidance application recalibrates (e.g., via control circuitry 304 (FIG. 3)) the calibration (e.g., stored at storage 308 (FIG. 3) and/or any location accessible via communications network 414 (FIG. 4)) at the recalibration rate. For example, in response to determining that the calibration of the input should be recalibrated once a week for user of the particular age of the user, the media guidance application may recalibrate an input, user input interface, and/or user profile associated with the user if the input, user input interface, and/or user profile has not been recalibrated within a week.

In some embodiments, the media guidance application may further indicate to a user when a recalibration should be performed. For example, in response to determining the calibration needs to be recalibrated, the media guidance application may notify the user. For example, the media guidance application may generate for display (e.g., via control circuitry 304 (FIG. 3)) one or more audio and/or video notifications that alert the user of the need to recalibrate. The media guidance application may then automatically, without a user input, recalibrate an input, user input interface, and/or user profile, or wait until a user requests the recalibration.

It is contemplated that the steps or descriptions of FIG. 5 may be used with any other embodiment of this disclosure. In addition, the steps and descriptions described in relation to FIG. 5 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one or more of the steps in FIG. 5.

Figure 6:
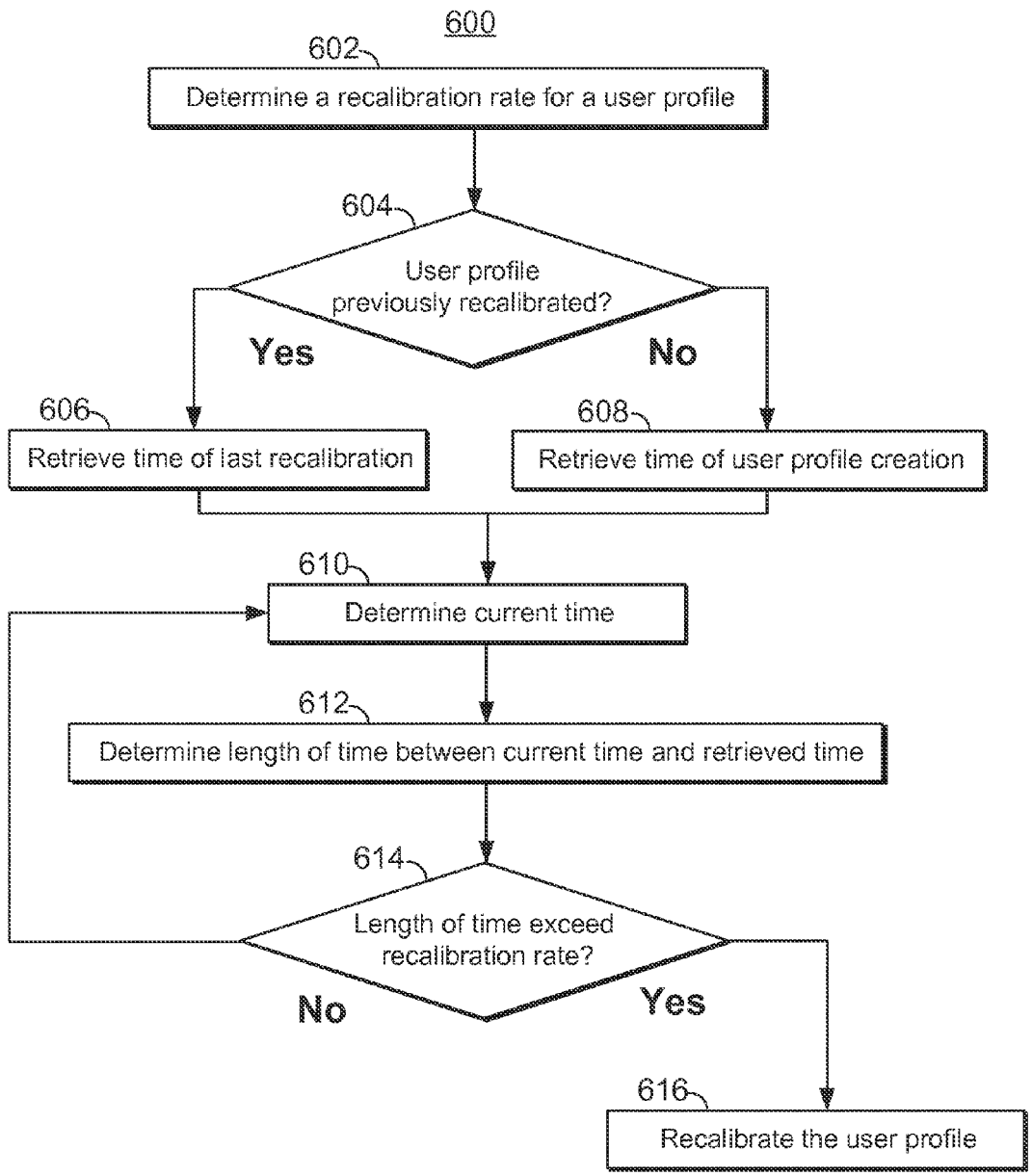
FIG. 6 is a flowchart of illustrative steps for determining whether or not a user profile should be recalibrated based on a determined recalibration rate in accordance with some embodiments of the disclosure.

FIG. 6 is a flowchart of illustrative steps for determining whether or not a user profile should be recalibrated based on a determined recalibration rate. It should be noted that process 600 or any step thereof could be performed on, or provided by, any of the devices shown in FIGS. 3-4. For example, process 600 may be executed by control circuitry 304 (FIG. 3) as instructed by a media guidance application implemented on user equipment 402, 404, and/or 406 (FIG. 4) in order to determine whether or not a user profile should be recalibrated based on a determined recalibration rate. In addition, one or more steps of process 600 may be incorporated into or combined with one or more steps of any other process or embodiment (e.g., as described in relation to FIGS. 5 and 7-8).

At step 602, the media guidance application determines (e.g., via control circuitry 304 (FIG. 3)) a recalibration rate for a user profile. For example, as discussed above in relation to step 506 (FIG. 5)), the media guidance application may cross-reference (e.g., using control circuitry 304 (FIG. 3)) the age of the user with a database (e.g., located at storage 308 (FIG. 3) and/or any location accessible via communications network 414 (FIG. 4)) listing recalibration rates at which inputs, user input interfaces, and/or user profiles need to be recalibrated for given ages to determine a recalibration rate at which to recalibrate a calibration of the user profile.

At step 604, the media guidance application determines (e.g., via control circuitry 304 (FIG. 3)) whether the user profile was previously recalibrated. For example, before determining whether or not a user profile has been recalibrated according to a determined recalibration rate, the media guidance application first determines whether or not the user profile has been previously recalibrated. If the media guidance application determines that the user profile has been previously recalibrated, the media guidance application proceeds to step 606. If the media guidance application determines that the user profile has not been previously recalibrated, the media guidance application proceeds to step 608.

At step 606, the media guidance application retrieves (e.g., from storage 308 (FIG. 3) and/or any location accessible via communications network 414 (FIG. 4)) a time of last recalibration. For example, the media guidance application may store a log related to previous recalibrations, including but not limited to, when the previous recalibrations occurred and how the user profile was recalibrated. The log may be stored in one or more locations (e.g., storage 308 (FIG. 3) and/or any other location accessible via communications network 414 (FIG. 4)).

At step 608, the media guidance application retrieves (e.g., from storage 308 (FIG. 3) and/or any location accessible via communications network 414 (FIG. 4)) a time of a user profile creation. For example, the media guidance application may store a log related to a user profile that includes but is not limited to, when the user profile was created and what calibrations are included in the user profile. The log may be stored in one or more locations (e.g., storage 308 (FIG. 3) and/or any other location accessible via communications network 414 (FIG. 4)).

At step 610, the media guidance application determines a current time. For example, as discussed above, the media guidance application may (e.g., in control circuitry 304 (FIG. 3)) incorporate and/or have access to a calendar and/or timekeeping function that may determine the current date. At step 612, the media guidance application may determine (e.g., via control circuitry 304 (FIG. 3)) a length of time between the current time and the time retrieved in step 606 or 608. For example, the media guidance application may compare (e.g., via control circuitry 304 (FIG. 3)) the date of the last recalibration or the date of the user profile creation (e.g., located in storage 308 (FIG. 3) and/or any location accessible via communications network 414 (FIG. 4)) to the current date to determine a length of time between the current time and the retrieved time.

For example, if the time retrieved (e.g., from storage 308 (FIG. 3)) by the media guidance application corresponds to Mar. 1, 2014, and the media guidance application determines that the current time corresponds to Mar. 15, 2014 (e.g., as determined by a calendar and/or timekeeping function accessible by control circuitry 304 (FIG. 3)), the media guidance application may determine that the length of time between the current time and the retrieved time is two weeks.

At step 614, the media guidance application determines (e.g., via control circuitry 304 (FIG. 3)) whether the length of time exceeds the recalibration rate. For example, if the recalibration rate may correspond to one recalibration per week. If the media guidance application determines the length of time between the current time and the retrieved time is one recalibration every two weeks (e.g., corresponding to a length of two weeks since the last recalibration), the media guidance application may determine that the length of time (e.g., two weeks) exceeds the recalibration rate (e.g., one week).

If the media guidance application determines (e.g., via control circuitry 304 (FIG. 3)) that the length of time exceeds the recalibration rate, the media guidance application proceeds to step 616 and recalibrate the user profile. In contrast, if the media guidance application determines (e.g., via control circuitry 304 (FIG. 3)) that the length of time does not exceed the recalibration rate, the media guidance application returns to step 610 and determines the current time. For example, the media guidance application may perform one or more iterations of process 600 (or a portion thereof), which results in the continuous or period recalibration of the user profile.

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one or more of the steps in FIG. 6.

Figure 7:
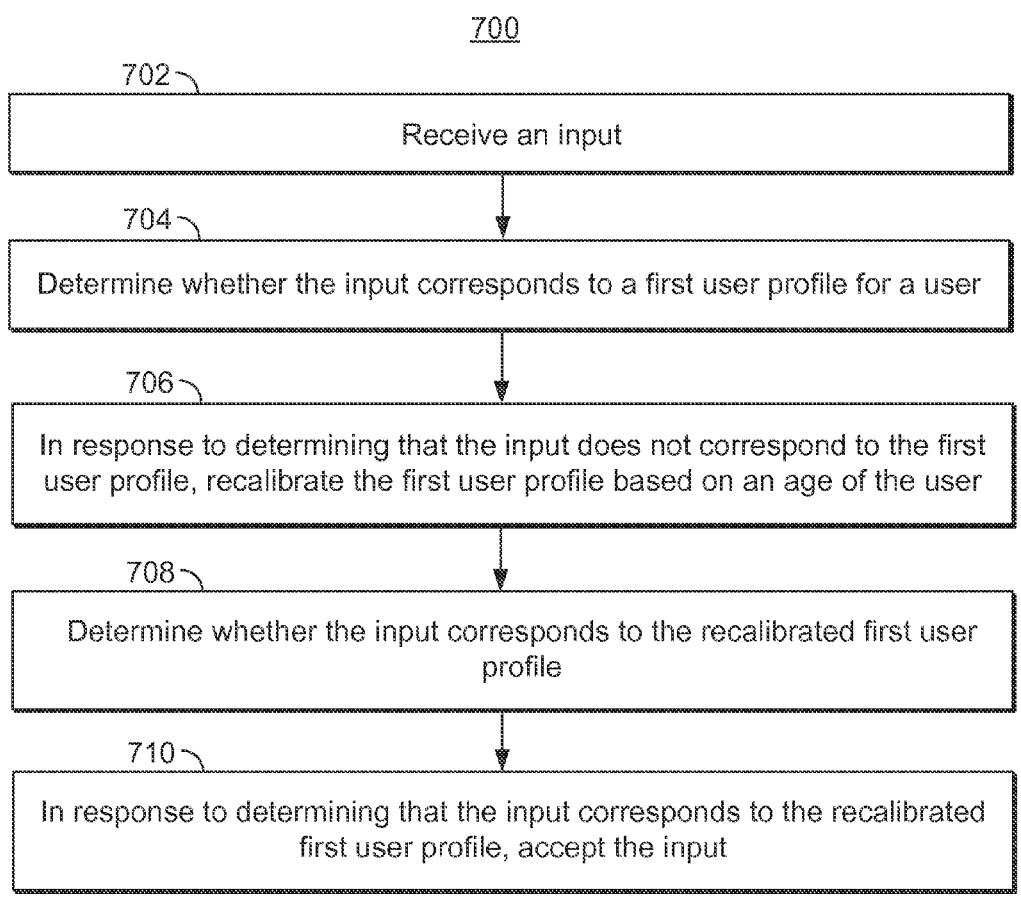
FIG. 7 is a flowchart of illustrative steps for determining whether an input corresponds to the recalibrated first user profile in accordance with some embodiments of the disclosure.

FIG. 7 is a flowchart of illustrative steps for determining whether an input corresponds to the recalibrated first user profile. It should be noted that process 700 or any step thereof could be performed on, or provided by, any of the devices shown in FIGS. 3-4. For example, process 700 may be executed by control circuitry 304 (FIG. 3) as instructed by a media guidance application implemented on user equipment 402, 404, and/or 406 (FIG. 4) in order to determine whether an input corresponds to the recalibrated first user profile. In addition, one or more steps of process 700 may be incorporated into or combined with one or more steps of any other process or embodiment (e.g., as described in relation to FIGS. 5-6 and 8).

At step 702, the media guidance application receives an input (e.g., via user input interface 310 (FIG. 3)). For example, the media guidance application may receive inputs via voice controls, motion controls, brain activity controls, etc., through one or more user input interfaces. Furthermore, the media guidance application may process (e.g., via control circuitry 304 (FIG. 3)) the inputs to determine measurements and/or other characteristics of the input.

For example, the media guidance application may compare the measurements and/or characteristics of the input to a database (e.g., located at storage 308 (FIG. 3) and/or any location accessible via communications network 414 (FIG. 4)) listing measurements and/or characteristics of inputs that correspond to particular media guidance application operations. Based on the comparison, the media guidance application may determine what media guidance application operation (if any) the input corresponds to.

At step 704, the media guidance application determines (e.g., via control circuitry 304 (FIG. 3)) whether or not the input corresponds to a first user profile for a first user (e.g., located at storage 308 (FIG. 3) and/or any location accessible via communications network 414 (FIG. 4)). For example, in addition to determining whether or not the input corresponds to a particular media guidance application operation, the media guidance application may compare (e.g., via control circuitry 304 (FIG. 3)) the input (or the measurements and/or characteristics associated with the input) to a user profile.

For example, an input (e.g., a voice command) may include one or more measurements and/or characteristics describing the input. For example, in the case of a voice command, a measurement and/or characteristic may indicate a particular accent, pronunciation, articulation, roughness, nasality, pitch, volume, and speed. For example, the media guidance application may compare the measurements and/or characteristics of the input to a database (e.g., located at storage 308 (FIG. 3) and/or any location accessible via communications network 414 (FIG. 4)) listing measurements and/or characteristics of inputs that correspond to a particular user associated with a user profile. Based on the comparison, the media guidance application may determine whether the input corresponds to the user associated with the user profile. For example, in the case of a voice control, the user profile may indicate a particular level of articulation associated with the user. If the media guidance application determines that the input (e.g., a voice command) did not have that particular level of articulation, the media guidance application may determine that the input was not received from the user associated with the user profile.

At step 706, the media guidance application, in response to determining (e.g., via control circuitry 304 (FIG. 3)) that the input does not correspond to the first user profile, may recalibrate the first user profile based on an age of the user. For example, in response to determining that there is a discrepancy in the accent, pronunciation, etc., between a received voice command and the correct accent, pronunciation, etc., in a user profile (e.g., causing the command or the user issuing the command to fail to be recognized), the media guidance application may recalibrate the user profile in order to alleviate the discrepancy.

For example, the media guidance application may store (e.g., in storage 308 (FIG. 3) and/or any location accessible via communications network 414 (FIG. 4)) a particular value and/or threshold range associated with an input (or a measurement and/or characteristic of an input) received from a user. The media guidance application may recalibrate the user profile such that the value and/or threshold range associated with the input in the first user profile is changed.

At step 708, the media guidance application determines (e.g., via control circuitry 304 (FIG. 3)) whether the input corresponds to the recalibrated first user profile. For example, in response to determining that the pitch of a received voice command differs from the pitch associated with voice commands in the first user profile, the media guidance application may recalibrate (e.g., via control circuitry 304 (FIG. 3)) the first user profile based on the age of the user. For example, the media guidance application may determine (e.g., via control circuitry 304 (FIG. 3)) that, based on the age of the user, the pitch in the user profile should be lowered. Accordingly, the media guidance application may lower (e.g., via control circuitry 304 (FIG. 3)) the pitch associated with voice commands in the first user profile. After which, the media guidance application may determine (e.g., via control circuitry 304 (FIG. 3)) whether the pitch of the received voice command corresponds to the lowered pitch associated with the recalibrated user profile.

At step 710, the media guidance application accepts the input in response to determining (e.g., via control circuitry 304 (FIG. 3)) that the input corresponds to the recalibrated first user profile. For example, in response to determining (e.g., via control circuitry 304 (FIG. 3)) that the pitch of the received voice command corresponds to the lowered pitch associated with the recalibrated user profile, the media guidance application performs (or causes to be performed) the received voice command. In contrast, the media guidance application may not accept the input in response to determining (e.g., via control circuitry 304 (FIG. 3)) that the input does not correspond to the recalibrated first user profile. For example, in response to determining that the pitch of the received voice command does not correspond to the lowered pitch associated with the recalibrated user profile, the media guidance application may not perform (or cause to be performed) the received voice command.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one or more of the steps in FIG. 7.

Figure 8:
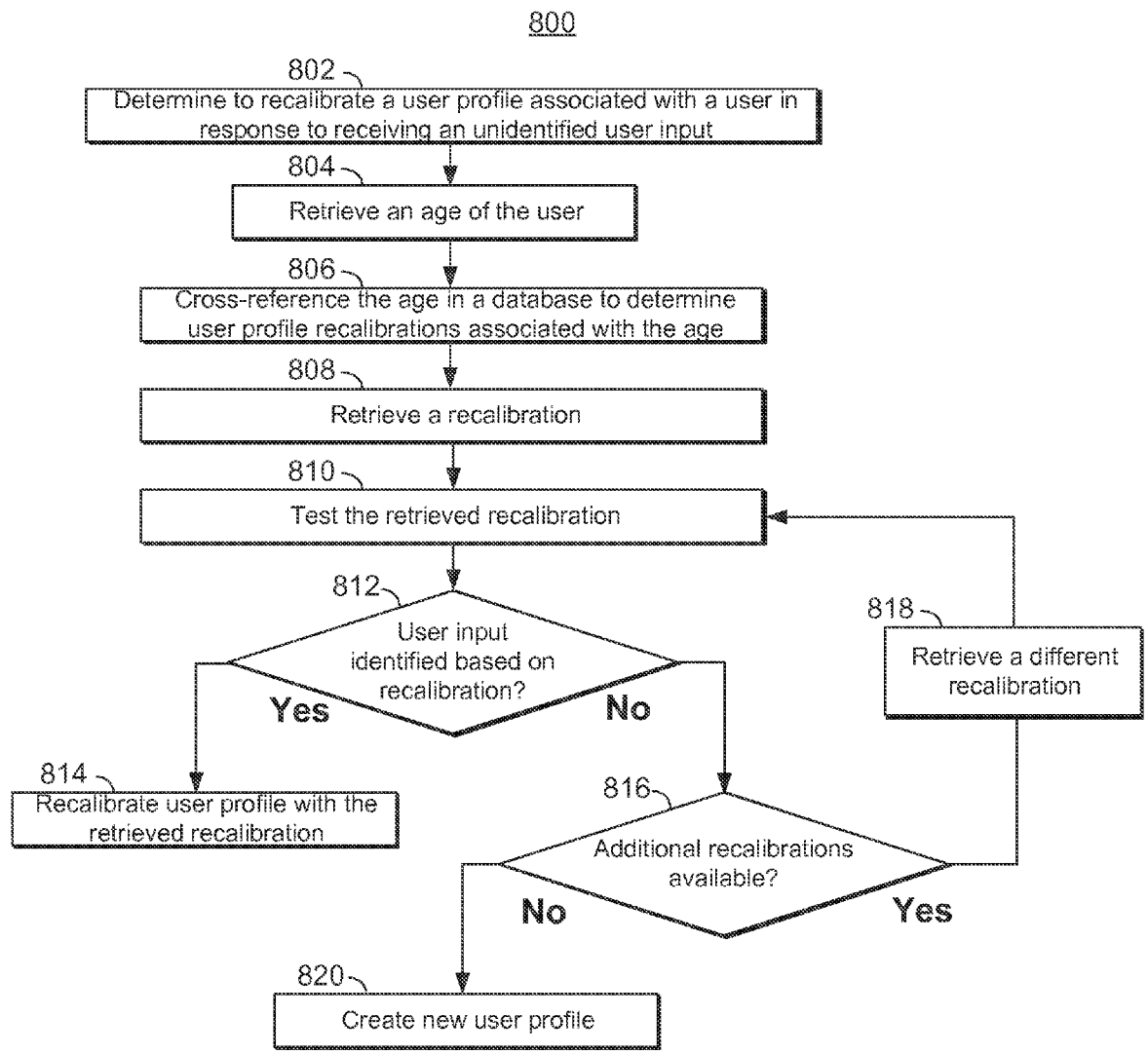
FIG. 8 is a flowchart of illustrative steps for determining whether or not a user profile should be recalibrated based on a determined recalibration rate in accordance with some embodiments of the disclosure.

FIG. 8 is a flowchart of illustrative steps for determining whether or not a user profile should be recalibrated based on a determined recalibration rate. It should be noted that process 800 or any step thereof could be performed on, or provided by, any of the devices shown in FIGS. 3-4. For example, process 800 may be executed by control circuitry 304 (FIG. 3) as instructed by a media guidance application implemented on user equipment 402, 404, and/or 406 (FIG. 4) in order to determine whether or not a user profile should be recalibrated based on a determined recalibration rate. In addition, one or more steps of process 800 may be incorporated into or combined with one or more steps of any other process or embodiment (e.g., as described in relation to FIGS. 5-7).

At step 802, the media guidance application determines to recalibrate a user profile associated with a user in response to receiving an unidentified user input. For example, as discussed above, the media guidance application, in response to determining (e.g., via control circuitry 304 (FIG. 3)) that an input does not correspond to a user profile, may recalibrate the user profile based on an age of the user. For example, in response to determining that there is a discrepancy in the accent, pronunciation, etc., between a received voice command and the correct accent, pronunciation, etc., in a user profile (e.g., causing the command or the user issuing the command to fail to be recognized), the media guidance application may recalibrate the user profile in order to alleviate the discrepancy.

At step 804, the media guidance application retrieves (e.g., via control circuitry 304 (FIG. 3)) an age of the user. For example, the media guidance application may (e.g., in control circuitry 304 (FIG. 3)) incorporate and/or have access to a calendar and/or timekeeping function that may determine the current date. The media guidance application may compare (e.g., via control circuitry 304 (FIG. 3)) the previously listed age and/or birth date of the user (e.g., stored in the user profile) to the current date to determine a current age of the user. For example, a previously listed age may be replaced with a new calculated age (e.g., based on the birth date of the user and the current date) or may be appended by adding a length of time corresponding to the amount of time from the current time to the time when the listed age was last updated to the listed age.

At step 806, the media guidance application cross-references (e.g., via control circuitry 304 (FIG. 3)) the age in a database (e.g., located at storage 308 (FIG. 3) and/or any location accessible via communications network 414 (FIG. 4)). For example, the media guidance application cross-references (e.g., using control circuitry 304 (FIG. 3)) the age of the user with a database (e.g., located at storage 308 (FIG. 3) and/or any location accessible via communications network 414 (FIG. 4)) listing recalibrations (e.g., what inputs need to be recalibrated and by what degree) associated with different ages. For example, in response to determining that a user is a particular age, the media guidance application may determine (e.g., via control circuitry 304 (FIG. 3)) the recalibration (if any) associated with inputs, user input interfaces, and/or user profiles associated with a user of that particular age.

At step 808, the media guidance application retrieves (e.g., from storage 308 (FIG. 3) and/or communications network 414 (FIG. 4)) a recalibration. For example, in response to determining that user is a particular age, the media guidance application may retrieve (e.g., via control circuitry 304 (FIG. 3)) the recalibration (if any) associated with inputs, user input interfaces, and/or user profiles associated with a user of that particular age. For example, the retrieved recalibration may indicate that the pitch of an input should be recalibrated.

At step 810, the media guidance application tests (e.g., via control circuitry 304 (FIG. 3)) the retrieved recalibration. For example, the media guidance application may compare a received input to the recalibrated input (e.g., based on the retrieved recalibration) of the user profile. The input may be recalibrated by requesting the user perform particular actions (e.g., speaking phrases, performing gestures, etc.) or may be recalibrated without requesting the user perform any particular actions (e.g., the media guidance application may automatically adjust the pitch of a calibration of an input based on the age of the user).

At step 812, the media guidance application determines whether the user input identifies the user input. If the media guidance application determines (e.g., via control circuitry 304 (FIG. 3)) that the user input is identified based on the recalibration, then the media guidance application proceeds to step 814. If the media guidance application determines (e.g., via control circuitry 304 (FIG. 3)) that the user input is not identified based on the recalibration, then the media guidance application proceeds to step 816.

For example, in response to determining that the enunciation of a received voice command differs from the enunciation associated with voice commands in the first user profile, the media guidance application may recalibrate (e.g., via control circuitry 304 (FIG. 3)) the first user profile based on the age of the user. For example, the media guidance application may determine (e.g., via control circuitry 304 (FIG. 3)) that, based on the age of the user, the enunciation in the user profile should be refined. Accordingly, the media guidance application may refine (e.g., via control circuitry 304 (FIG. 3)) the enunciation associated with voice commands in the first user profile. After which, the media guidance application may determine (e.g., via control circuitry 304 (FIG. 3)) whether the enunciation of the received voice command corresponds to the refined enunciation associated with the recalibrated user profile.

For example, before performing a command, the media guidance application may determine whether or not the user input is associated with a particular user or whether the user input is associated with a particular function. If the command does not correspond to a particular user (e.g., associated with a current user profile) or the command does not correspond to any available function, the media guidance application may proceed to step 816. Alternatively, if the command does correspond to a particular user (e.g., associated with a current user profile) or the command does correspond to any available function, the media guidance application may proceed to step 814.

At step 814, the media guidance application recalibrates (e.g., via control circuitry 304 (FIG. 3)) the user profile with the retrieved recalibration. For example, if the command does correspond to a particular user (e.g., associated with a current user profile) or the command does correspond to any available function based on the recalibration, the media guidance application updates the user profile such that future user inputs with also be accepted.

At step 816, the media guidance application determines whether or not there are additional recalibrations available. For example, if the command does not correspond to a particular user (e.g., associated with a current user profile) or the command does not correspond to any available function based on the recalibration, the media guidance application may search for additional recalibrations that may be applied. For example, if a recalibration of the pitch associated with a user profile does not result in an identified user input, the media guidance application may additionally or alternatively recalibrate the accent of the user profile. If there are additional recalibrations available, the media guidance application proceeds to step 818, and retrieves a different recalibration before returning to step 810.

If there are no additional recalibrations available, the media guidance application proceeds to step 820, and creates a new user profile. For example, in response to not being able to identify the user input, the media guidance application may designate the current user as a new user. Some embodiments, upon detecting a new user (e.g., a user not associated with a user profile), the media guidance application may create (e.g., via control circuitry 304 (FIG. 3)) a user profile associated with that user. In such cases, the media guidance application may obtain information about the user such as the name, age, birth date, and/or any other relevant data, as well as obtaining initial or default calibrations of various inputs and/or user input interfaces to associate with the new user profile.

It is contemplated that the steps or descriptions of FIG. 8 may be used with any other embodiment of this disclosure. In addition, the steps and descriptions described in relation to FIG. 8 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 3-4 could be used to perform one or more of the steps in FIG. 8.

The above-described embodiments of the present disclosure are presented for purposes of illustration and not of limitation, and the present disclosure is limited only by the claims that follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted, the systems and/or methods described above may be applied to, or used in accordance with, other systems and/or methods.

What is claimed is:

1. A method of customizing user controls, the method comprising:
    storing a calibration of an input for a user;
    determining a biological age of the user by comparing a birth date of the user with a current date;
    searching, based on the age of the user, a database listing recalibration rates at which inputs need to be recalibrated for given biological ages to determine a recalibration rate at which to recalibrate the calibration, wherein the recalibration rate indicates a frequency for recalibrating the stored calibration and a degree for updating an attribute of the stored calibration of the user;
    receiving verbal input from the user;
    determining that the received verbal input does not correspond to any available media guidance application operations; and
    in response to determining that the received verbal input does not correspond to any available media guidance application operations, recalibrating the calibration based on the frequency and degree indicated by the recalibration rate.

2. The method of claim 1, further comprising:
    determining a length of time since a previous recalibration; and
    comparing the recalibration rate to the length of time to determine whether the calibration needs to be recalibrated.

3. The method of claim 2, further comprising, in response to determining the calibration needs to be recalibrated, notifying the user.

4. The method of claim 1, wherein the calibration is automatically recalibrated.

5. The method of claim 1, wherein the input is a voice control input.

6. The method of claim 5, wherein the recalibration rate corresponds to a rate at which a voice of the user changes at the age of the user.

7. The method of claim 1, wherein the input is a motion control input.

8. The method of claim 7, wherein the recalibration rate corresponds to a rate at which coordination of the user changes at the age of the user.

9. The method of claim 1, wherein the input is based on brain activity of the user.

10. The method of claim 9, wherein the recalibration rate corresponds to a rate at which brain activity of the user changes at the age of the user.

11. A system for customizing user controls, the system comprising:
    storage circuitry configured to store a calibration of an input for a user; and
    control circuitry configured to:
        determine a biological age of the user by comparing a birth date of the user with a current date;
        search, based on the age of the user, a database listing recalibration rates at which inputs need to be recalibrated for given biological ages to determine a recalibration rate at which to recalibrate the calibration, wherein the recalibration rate indicates a frequency for recalibrating the stored calibration and a degree for updating an attribute of the stored calibration of the user;
        receiving verbal input from the user;
        determining that the received verbal input does not correspond to any available media guidance application operations; and
        in response to determining that the received verbal input does not correspond to any available media guidance application operations, recalibrate the calibration based on the frequency and degree indicated by the recalibration rate.

12. The system of claim 11, wherein the control circuitry is further configured to:
    determine a length of time since a previous recalibration; and compare the recalibration rate to the length of time to determine whether the calibration needs to be recalibrated.

13. The system of claim 12, wherein the control circuitry is further configured to notify the user that the calibration needs to be recalibrated.

14. The system of claim 11, wherein the calibration is automatically recalibrated.

15. The system of claim 11, wherein the input is a voice control input.

16. The system of claim 15, wherein the recalibration rate corresponds to a rate at which a voice of the user changes at the age of the user.

17. The system of claim 11, wherein the input is a motion control input.

18. The system of claim 17, wherein the recalibration rate corresponds to a rate at which coordination of the user changes at the age of the user.

19. The system of claim 11, wherein the input is based on brain activity of the user.

20. The system of claim 19, wherein the recalibration rate corresponds to a rate at which brain activity of the user changes at the age of the user.

* * * * *